US009848903B2

(12) United States Patent
Tsubuku et al.

(10) Patent No.: US 9,848,903 B2
(45) Date of Patent: Dec. 26, 2017

(54) ULTRASONIC TREATMENT APPARATUS

(71) Applicant: OLYMPUS CORPORATION, Hachioji-shi, Tokyo (JP)

(72) Inventors: Yoshihiro Tsubuku, Fuchu (JP); Minoru Kawasaki, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 15/443,829

(22) Filed: Feb. 27, 2017

(65) Prior Publication Data
US 2017/0164974 A1 Jun. 15, 2017

Related U.S. Application Data

(63) Continuation of application No. 15/100,046, filed as application No. PCT/JP2015/052867 on Feb. 2, 2015.

(30) Foreign Application Priority Data

Feb. 17, 2014 (JP) ................ 2014-027989

(51) Int. Cl.
*A61N 7/00* (2006.01)
*A61B 17/32* (2006.01)
(Continued)

(52) U.S. Cl.
CPC .... *A61B 17/320092* (2013.01); *A61B 17/282* (2013.01); *A61B 17/320068* (2013.01);
(Continued)

(58) Field of Classification Search
None
See application file for complete search history.

(56) References Cited

U.S. PATENT DOCUMENTS

2010/0168742 A1\* 7/2010 Shibata .......... A61B 17/320068
606/42
2012/0265196 A1 10/2012 Turner et al.
(Continued)

FOREIGN PATENT DOCUMENTS

EP 1820460 A2 8/2007
EP 1842502 A1 10/2007
(Continued)

OTHER PUBLICATIONS

Dec. 1, 2015 Office Action issued in Japanese Patent Application No. 2015-542089.
(Continued)

*Primary Examiner* — Joel F Brutus
(74) *Attorney, Agent, or Firm* — Oliff PLC

(57) ABSTRACT

An ultrasonic treatment apparatus includes a movement unit moving in accordance with at least one of an acting state of a load to a treatment section from a jaw and an opening angle of the jaw relative to the treatment section, a movement detector detecting a moving state of the movement unit, and a peak detecting section detecting a target peak of an ultrasonic impedance value. The ultrasonic treatment apparatus includes a control section controlling the peak detecting section to a detection disallowed state where a detection of the target peak is not executed when the movement unit is not placed within a prescribed range based on a detection result in the movement detector.

12 Claims, 16 Drawing Sheets

(51) Int. Cl.
*A61B 17/28* (2006.01)
*A61B 17/00* (2006.01)
(52) U.S. Cl.
CPC ...... *A61N 7/00* (2013.01); *A61B 2017/00106* (2013.01); *A61N 2007/0086* (2013.01)

(56) References Cited

U.S. PATENT DOCUMENTS

| | | | |
|---|---|---|---|
| 2012/0310264 A1 | 12/2012 | Messerly et al. | |
| 2013/0267975 A1* | 10/2013 | Timm ............ | A61B 17/320068 606/169 |
| 2014/0031809 A1* | 1/2014 | Takabayashi .. | A61B 17/320092 606/33 |

FOREIGN PATENT DOCUMENTS

| | | |
|---|---|---|
| JP | 2007-229454 A | 9/2007 |
| JP | 2007-275291 A | 10/2007 |
| JP | 2009-261935 A | 11/2009 |
| JP | 2012-533346 A | 12/2012 |
| JP | 2013-031669 A | 2/2013 |
| JP | 5379931 B1 | 12/2013 |

OTHER PUBLICATIONS

Apr. 21, 2015 International Search Report issued in PCT/JP2015/052867.
Apr. 21, 2015 Written Opinion issued in PCT/JP2015/052867.
Sep. 1, 2016 International Preliminary Report on Patentability issued in PCT/JP2015/052867.
Dec. 7, 2016 Office Action issued in U.S. Appl. No. 15/100,046.
Sep. 29, 2017 Extended European Search Report issued in European Patent Application No. 15748810.7.

\* cited by examiner

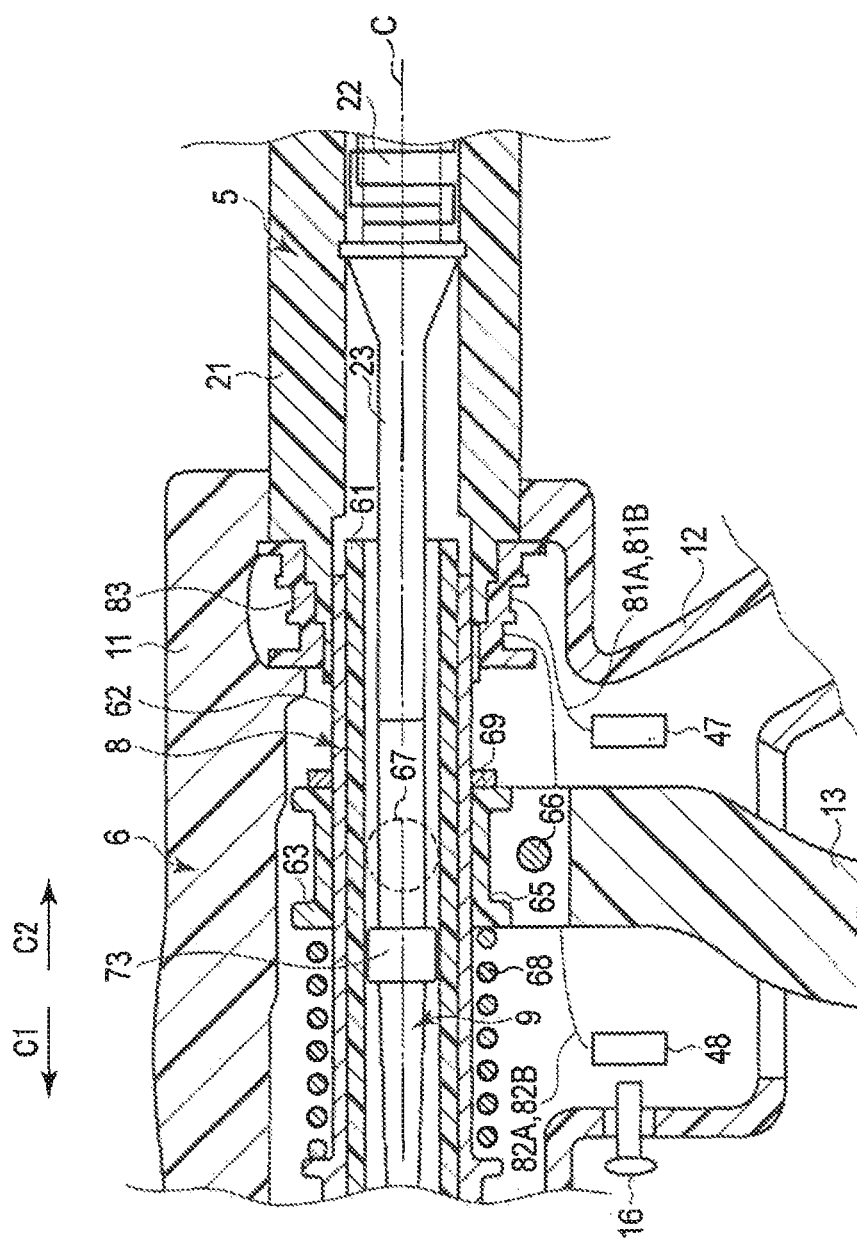
F I G. 2

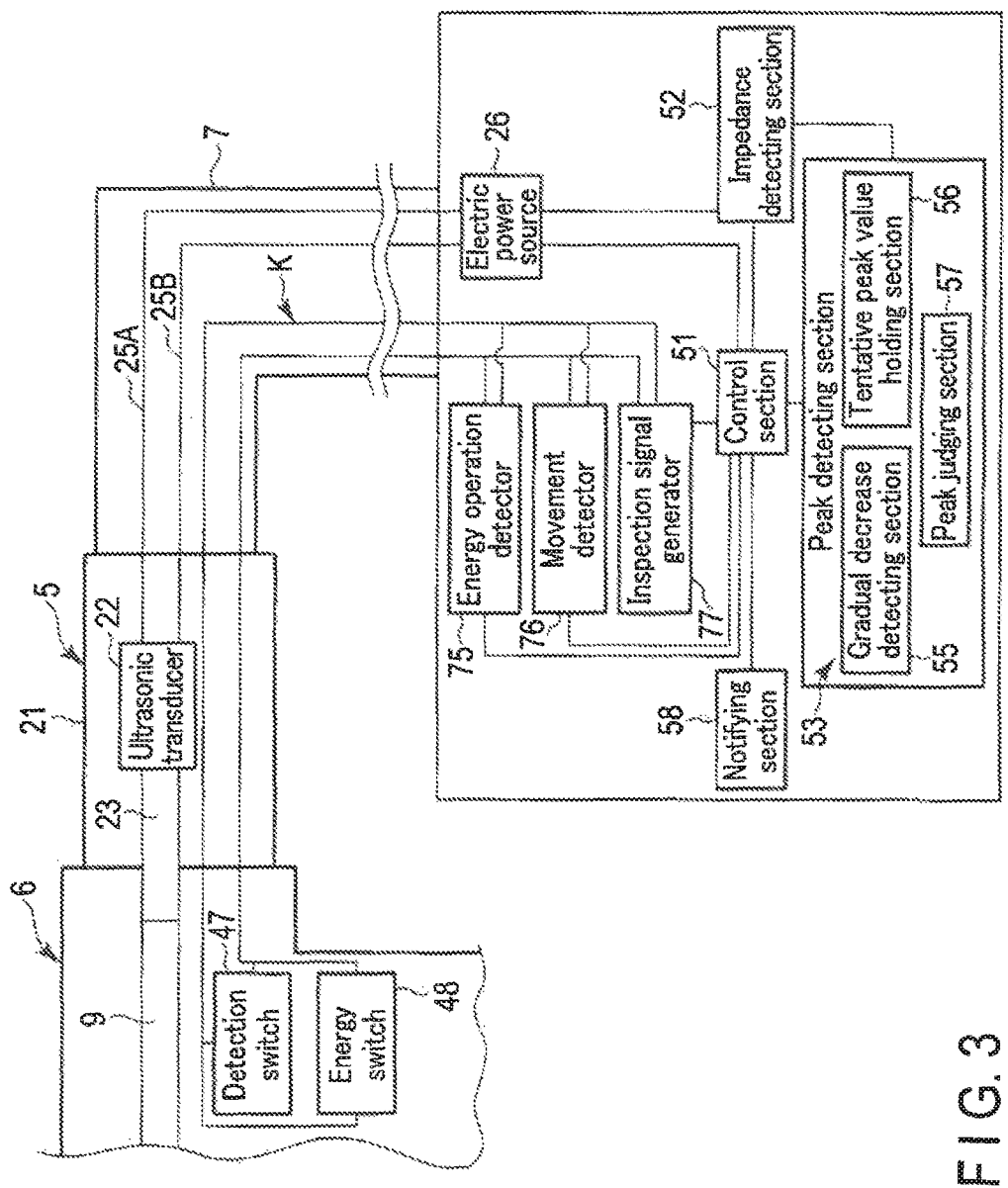
F I G. 3

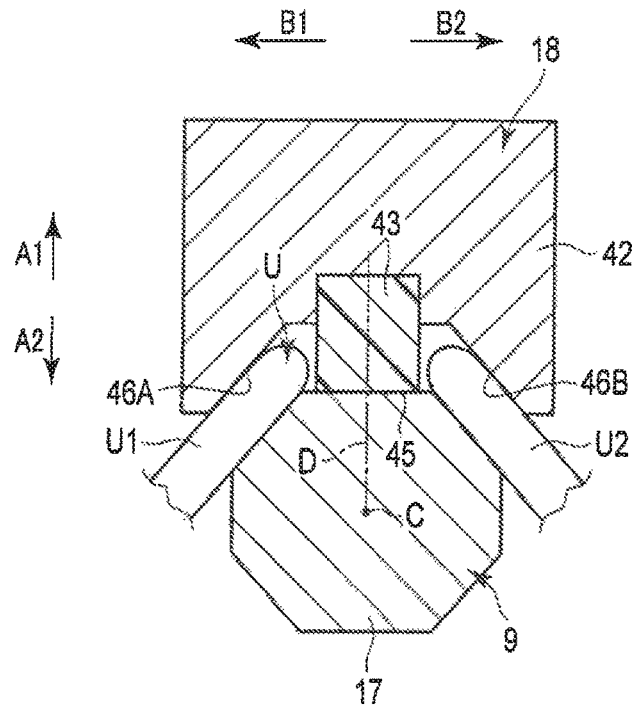
F I G. 12
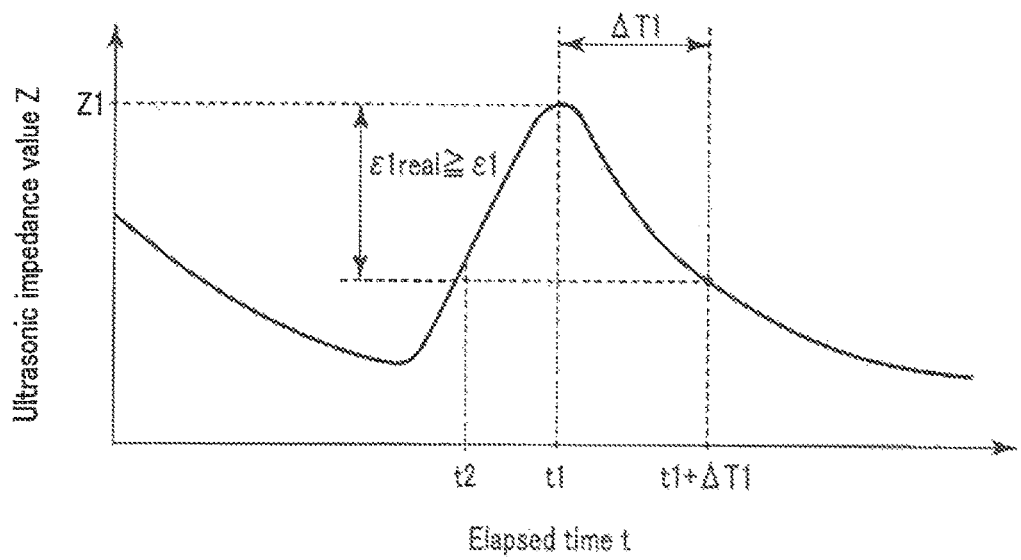
F I G. 13

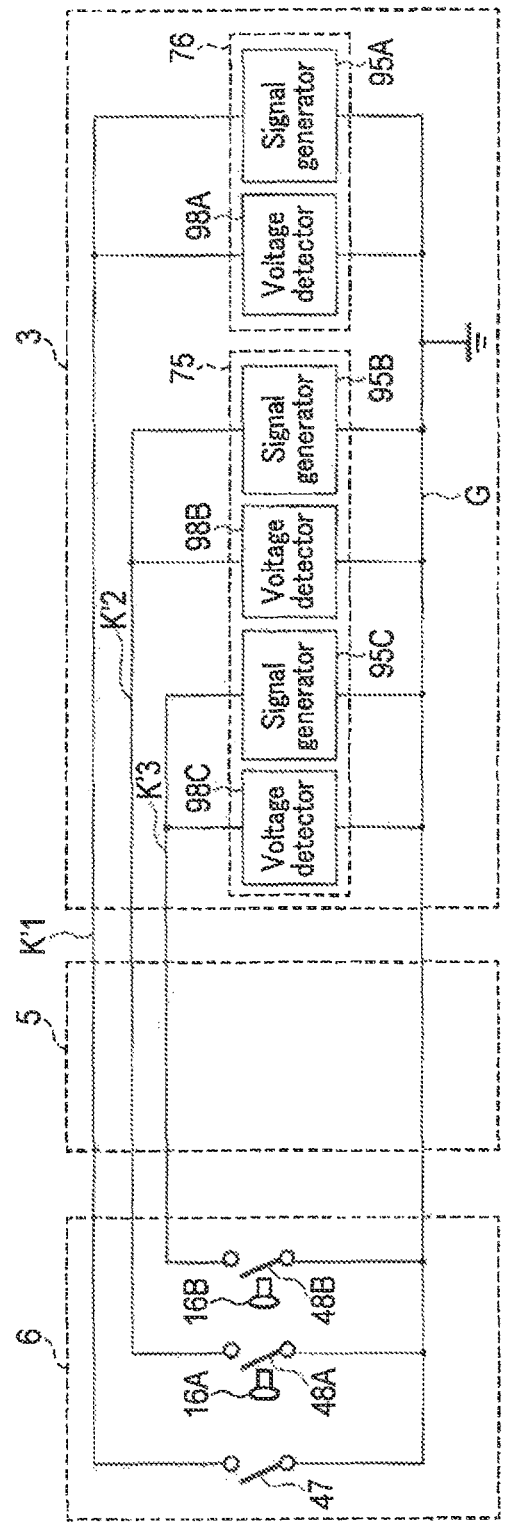
F I G. 19

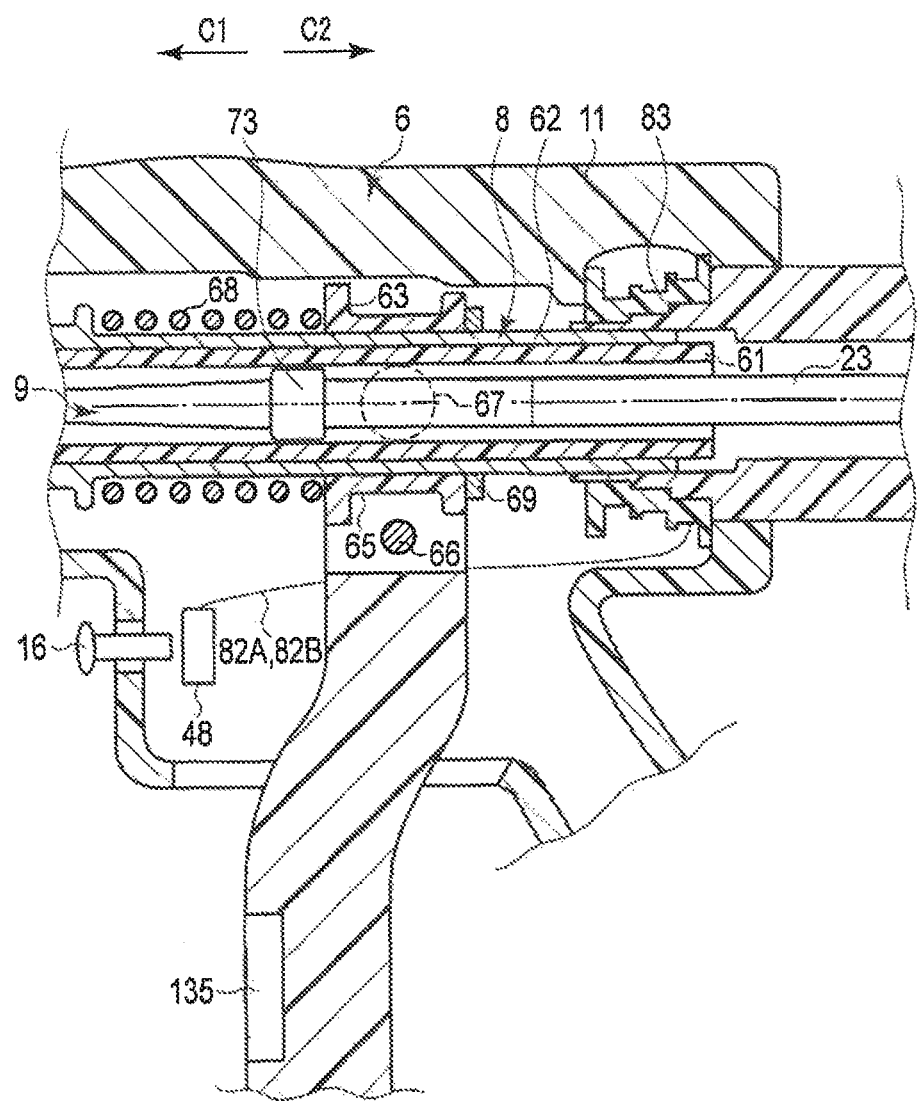
F I G. 22

ULTRASONIC TREATMENT APPARATUS

CROSS-REFERENCE TO RELATED APPLICATIONS

This is a Continuation of application Ser. No. 15/100,046 filed May 27, 2016, which in turn is a National Stage of PCT Application No. PCT/JP2015/052867, filed Feb. 2, 2015 and based upon and claiming the benefit of priority from prior Japanese Patent Application No. 2014-027989, filed Feb. 17, 2014. The disclosure of the prior applications is hereby incorporated by reference herein in its entirety

BACKGROUND OF THE INVENTION

1. Field of the Invention

The present invention relates to an ultrasonic treatment apparatus which grasps a treated target between a treatment section to which an ultrasonic vibration is transmitted and a jaw openable and closable relative to the treatment section, so as to treat the grasped treated target by use of the ultrasonic vibration.

2. Description of the Related Art

For example, U.S. Patent Application Publication No. 2012/0310264 discloses an ultrasonic treatment apparatus which includes a treatment section to which an ultrasonic vibration is transmitted and a jaw openable and closable relative to the treatment section. In this ultrasonic treatment apparatus, when vibration generating electric power is transmitted from an electric power source to a vibration generating section, the ultrasonic vibration is generated in an ultrasonic transducer which the vibration generating section. Then, the generated ultrasonic vibration is transmitted to the treatment section, and the treatment section treats a treated target such as a biological tissue by use of the transmitted ultrasonic vibration. Here, opening and closing directions of the jaw are perpendicular (transverse) to a transmitting direction of the ultrasonic vibration. When the ultrasonic vibration is transmitted to the treatment section in a state where the treated target is grasped between the treatment section and the jaw, frictional heat is generated between the treated target and the treatment section. By the frictional heat, the treated target is coagulated and simultaneously incised. Furthermore, in the ultrasonic treatment apparatus, an ultrasonic impedance value of the vibration generating electric power is detected with time, and it is judged whether the ultrasonic impedance value is within a range of a first default threshold or more and a second default threshold or less, the second threshold being greater than the first threshold.

BRIEF SUMMARY OF THE INVENTION

According to one aspect of the invention, An ultrasonic treatment apparatus includes that: an electric power source configured to output a vibration generating electric power; a vibration generating section configured to generate an ultrasonic vibration when the vibration generating electric power is supplied from the electric power source; a treatment section to which the ultrasonic vibration generated in the vibration generating section is transmitted, and which is configured to perform a treatment by use of the transmitted ultrasonic vibration; a jaw that is openable and closable relative to the treatment section, and includes a contact portion contactable with the treatment section in a state where the jaw is closed relative to the treatment section, an acting state of a load to the treatment section from the jaw changing in accordance with an opening or closing movement relative to the treatment section; a movement unit that is configured to move in accordance with at least one of the acting state of the load to the treatment section from the jaw and an opening angle of the jaw relative to the treatment section; a movement detector which is configured to detect a moving state of the movement unit; an impedance detecting section which is configured to detect an ultrasonic impedance value of the vibration generating electric power with time, in a state where the vibration generating electric power is output from the electric power source; a gradual decrease detecting section which is configured to detect a gradual decrease start point to start gradual decrease of the ultrasonic impedance value on the basis of detection results in the impedance detecting section; a tentative peak value holding section which is configured to hold the ultrasonic impedance value at the detected gradual decrease start point as a tentative peak value; a peak judging section which is configured to judge whether or not the held tentative peak value is a target peak of a detection target by comparing, with respect to the held tentative peak value, changes with time of the ultrasonic impedance value after the gradual decrease start point; and a control section which is configured to control the gradual decrease detecting section, the tentative value holding section, and the peak judging section to a detection disallowed state where a detection of the target peak is not executed when the movement unit is not placed within a prescribed range based on a detection result of the moving state of the movement unit in the movement detector.

Advantages of the invention will be set forth in the description which follows, and in part will be obvious from the description, or may be learned by practice of the invention. The advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 2 is a longitudinal cross-sectional view schematically showing configurations of the inside of a handle unit and the inside of a transducer unit according to the first embodiment;

FIG. 3 is a schematic view showing an electrical connection state of the handle unit, the transducer unit, and a control unit according to the first embodiment;

FIG. 12 is a schematic view explaining cut-and-divided of a treated target grasped between the treatment section and the jaw according to the first embodiment;

FIG. 13 is a schematic view showing an example of changes with time of an ultrasonic impedance value from start of output of a vibration generating electric power from the electric power source according to the first embodiment;

FIG. 19 is a schematic view showing a signal path of a digital signal according to a second modification;

FIG. 22 is a longitudinal cross-sectional view schematically showing configurations of the inside of the handle unit and the inside of the transducer unit according to a first reference example.

DETAILED DESCRIPTION OF THE INVENTION

First Embodiment

Figure 1:
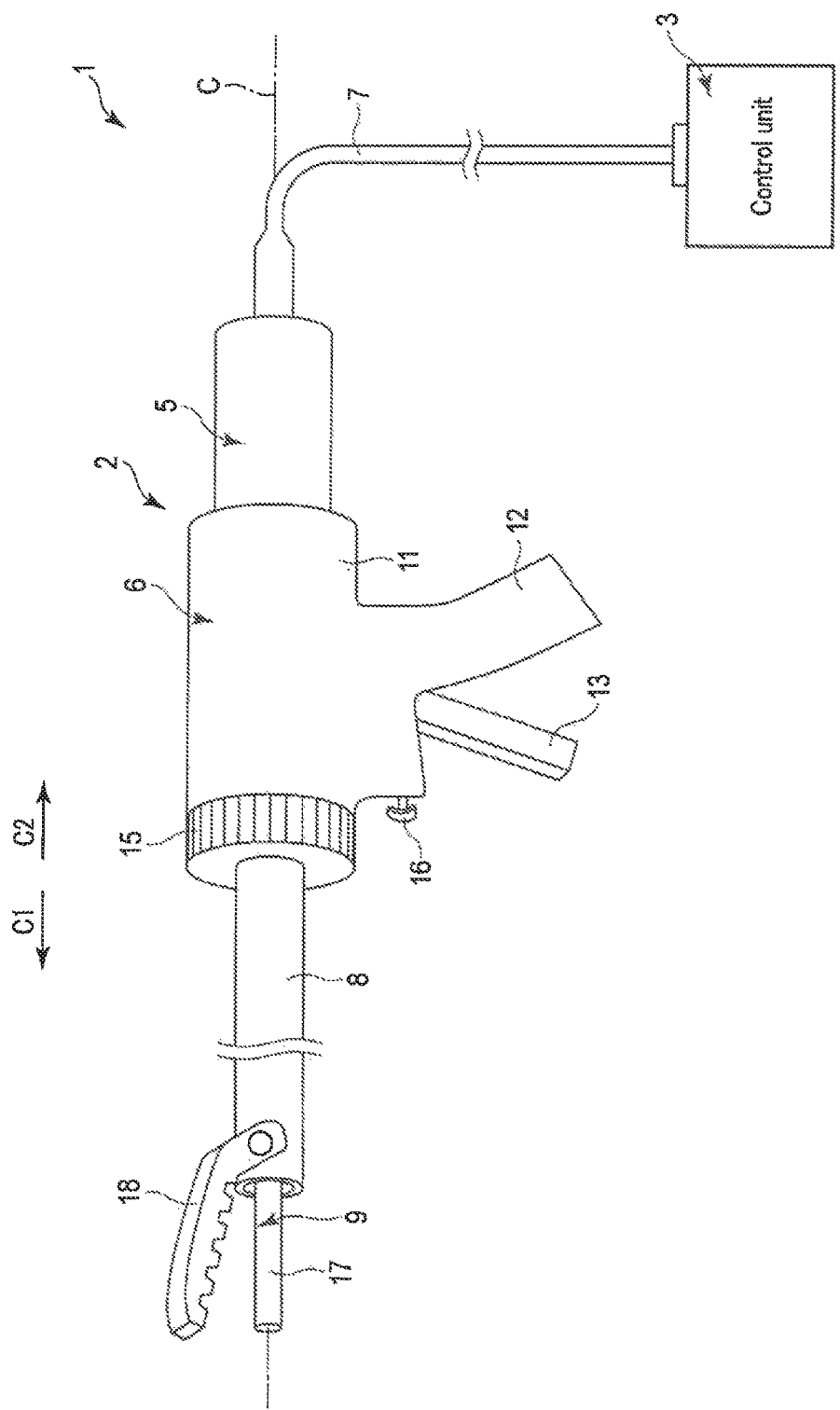
FIG. 1 is a schematic view showing an ultrasonic treatment apparatus according to a first embodiment of the present invention.

A first embodiment according to the present invention will now be described with reference to FIG. 1 to FIG. 7. FIG. 1 is a view showing an ultrasonic treatment apparatus 1. As shown in FIG. 1, the ultrasonic treatment system 1 includes an ultrasonic treatment instrument (a hand piece) 2, and a control unit (an energy control device) 3. The ultrasonic treatment tool 2 has a longitudinal axis C. One of two directions parallel to the longitudinal axis C is a distal direction (a direction of an arrow C1 in FIG. 1), and an opposite direction of the distal direction is a proximal direction (a direction of an arrow C2 in FIG. 1). The ultrasonic treatment instrument 2 includes a transducer unit 5 and a handle unit 6. The vibrator unit 5 is detachably coupled with a proximal direction side of the handle unit 6. One end of a cable 7 is connected to a proximal portion of the transducer unit 5. The other end of the cable 7 is connected to the control unit 3.

The handle unit 6 includes a tubular case portion 11 extended along the longitudinal axis C, a fixed handle 12 integrally formed with the tubular case portion 11, and a movable handle 13 coupled to the tubular case portion 11 to allow its turning motion. The fixed handle 12 is extended in a state that it is apart from the tubular case portion 11 to the longitudinal axis C. When the movable handle 13 turns around a position at which it is attached to the tubular case portion 11, the movable handle 13 opens or closes relative to the fixed handle 12. Further, the handle unit 6 includes a rotary operation knob 15 attached on a distal direction side of the tubular case portion 11. The rotary operation knob 15 can rotate around the longitudinal axis C relative to the tubular case portion 11. Furthermore, an energy operation input button 16 which an energy operation input section is provided to the fixed handle 12.

The ultrasonic treatment instrument 2 includes a sheath 8 extended along the longitudinal axis C. When the sheath 8 is inserted into the rotary operation knob 15 and into the tubular case portion 11 from the distal direction side, the sheath 8 is attached to the handle unit 6. Moreover, the ultrasonic treatment instrument 2 includes an ultrasonic probe 9. The ultrasonic probe 9 is extended along the longitudinal axis C from the inside of the tubular case portion 11 through an inside of the sheath 8. The ultrasonic probe 9 is inserted through the sheath 8. A treatment section 17 protruding from a distal end of the sheath 8 toward the distal direction is provided in a distal portion of the ultrasonic probe 9. Additionally, a jaw 18 is turnably attached in the distal portion of the sheath 8.

FIG. 2 is a view showing configurations of the inside of the handle unit 6 and the inside of the transducer unit 5. Further, FIG. 3 is a view showing an electrical connection state in the handle unit 6, the transducer unit 5, and the control unit 3. As shown in FIG. 2, the transducer unit 5 includes a transducer case 21. When the vibrator case 21 is inserted into the tubular case portion 11 from the proximal direction side, the vibrator unit 5 is attached to the handle unit 6.

Figure 4:
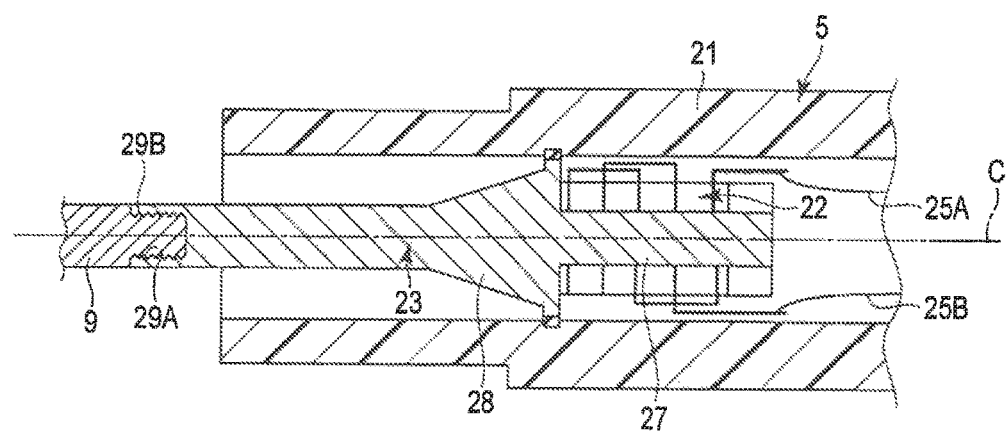
FIG. 4 is a longitudinal cross-sectional view schematically showing a configuration of the transducer unit according to the first embodiment.

FIG. 4 is a view showing a configuration of the transducer unit 5. As shown in FIG. 2 to FIG. 4, the transducer unit 5 includes the transducer e an ultrasonic transducer 22 which is a vibration generating section provided inside the vibrator case 21, and a horn member 23 to which the ultrasonic vibrator 22 is attached. One end of each of electrical wiring portions 25A and 25B is connected to the ultrasonic oscillator 22. The control unit 3 includes an electric power source 26 that can output a vibration generating electric power P. In the electric power source 26, for example, an electric power from, e.g., a receptacle outlet is converted into the vibration generating electric power P by a conversion circuit or the like, and the vibration generating electric power P is output. The other end of each of the electrical wiring portions 25A and 25B is connected to the electric power source 26. The vibration generating electric power P output from the electric power source 26 is supplied to the ultrasonic transducer 22 through the electrical wiring portions 25A and 25B.

When the vibration generating electric power P is supplied, an ultrasonic vibration produced in the ultrasonic transducer 22.

A transducer mounting portion 27 to which the ultrasonic transducer 2 mounted is provided to the horn member 23. The ultrasonic vibration produced by the ultrasonic vibrator 22 is transmitted to the horn member 23. Furthermore, a sectional area change portion 28 is provided to the horn member 23 on the distal direction side with respect to the transducer mounting portion 27. In the sectional area change portion 28, a sectional area perpendicular to the longitudinal axis C decreases toward the distal direction. The sectional area change portion 28 enlarges an amplitude of the ultrasonic vibration. A female screw portion 29A is provided in a distal portion of the horn member 23. Moreover, a male screw portion 298 is provided in a proximal portion of the ultrasonic probe 9. When the male screw portion 298 is screwed into the female screw portion 29A, the ultrasonic probe 9 is connected to the distal direction side of the horn member 23. The ultrasonic probe 9 is connected to the horn member 23 inside the tubular case portion 11.

The ultrasonic vibration transmitted to the horn member 23 is transmitted from the proximal direction toward the distal direction along the longitudinal axis C in the horn member 23 and the ultrasonic probe 9. That is, the horn member 23 and the ultrasonic probe 9 are a vibration transmitting portion configured to transmit the generated ultrasonic vibration. The ultrasonic vibration is transmitted toward the distal direction until it reaches the treatment section 17. The treatment section 17 gives a treatment to, e.g., a biological tissue by using the transmitted ultrasonic vibration. It is to be noted that, in the vibration transmitting portion (the horn member 23 and the ultrasonic probe 9), the proximal end (the proximal end of the horn member 23) and the distal end (the distal end of the ultrasonic probe 9) are antinode positions of the ultrasonic vibration. Additionally, the ultrasonic vibration is longitudinal vibration whose vibrating direction and whose transmitting direction are parallel to the longitudinal axis C (the longitudinal axial direction). Thus, the distal direction parallel to the longitudinal axis C is the transmitting direction of the ultrasonic vibration.

Figure 5:
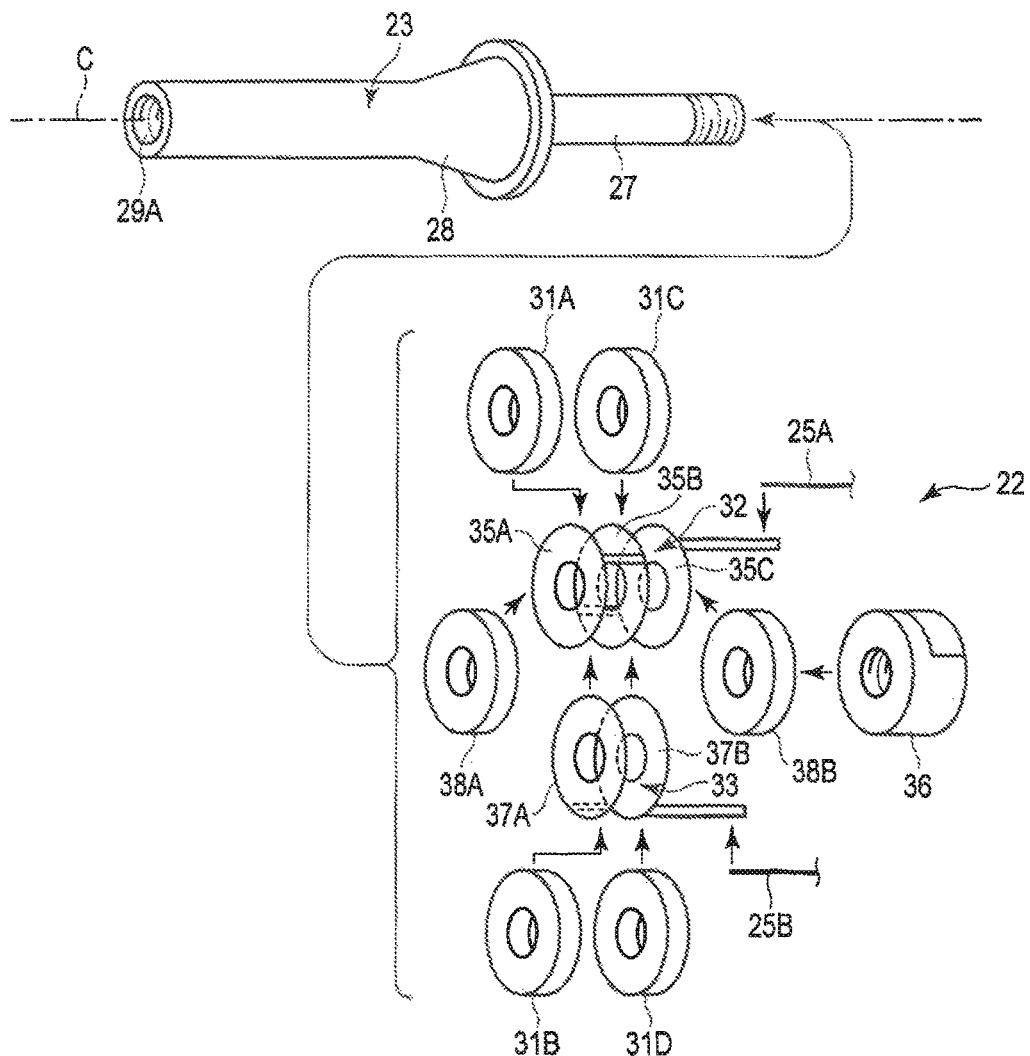
FIG. 5 is a schematic exploded perspective view showing each member in a horn member and an ultrasonic transducer according to the first embodiment.

FIG. 5 is an exploded view showing each member in the horn member 23 and the ultrasonic transducer 22. As shown in FIG. 5, the ultrasonic vibrator 22 includes (four in this embodiment) ring-like piezoelectric elements 31A to 31D. The vibrator mounting portion 27 of the horn member 23 is inserted through the respective piezoelectric elements 31A to 31D. Further, the respective piezoelectric elements 313 to 31D are disposed on the transducer mounting portion 27 in a state that each of their thickness direction is parallel to the transmitting direction of the ultrasonic vibration (i.e., the longitudinal axis C) and each of their radial direction is perpendicular to the transmitting direction of the ultrasonic vibration (i.e., the distal end direction).

The ultrasonic oscillator 22 includes a first electrode portion 32 and a second electrode portion 33. One end of the electrical wiring portion 25A is connected to the first electrode portion 32, and one end of the electrical wiring portion 25B is connected to the second electrode portion 33. The first electrode portion 32 includes first electrode ring portions 35A to 35C. The first electrode ring portion 35A is placed on the distal direction side of the piezoelectric element 31A, and the first electrode ring portion 35B is placed between the piezoelectric element 31B and the piezoelectric element 31C in the longitudinal axial direction parallel to the longitudinal axis C. Furthermore, the first electrode ring unit 35C is placed on the proximal direction side of the piezoelectric element 31D. The transducer mounting portion 27 is inserted through the respective first electrode ring portions 35A to 35C.

The second electrode portion 33 includes second electrode ring portions 37A and 37B. The second electrode ring portion 37A is placed between the piezoelectric element 31A and the piezoelectric element 31B in the longitudinal axial direction parallel to the longitudinal axis C. Moreover, the second electrode ring portion 37B is placed between the piezoelectric element 31C and the piezoelectric element 31D in the longitudinal axial direction. The vibrator mounting unit 27 is inserted through the respective second electrode ring portions 37A and 37B.

With the above-described configuration, the piezoelectric element 31A is held between the first electrode ring portion 35A and the second electrode ring portion 37A, and the piezoelectric element 31B is sandwiched between the second electrode ring portion 37A and the first electrode ring portion 35B. Additionally, the piezoelectric element 31C is held between the first electrode ring portion 35B and the second electrode ring portion 37B, and the piezoelectric element 31D is held between the second electrode ring portion 37B and the first electrode ring portion 35C. Thus, the respective piezoelectric elements 31A to 31D are held between the first electrode portion 32 and the second electrode portion 33.

Further, the ultrasonic transducer 22 includes insulation rings 38A and 38B. The insulation ring 38A is placed on the distal direction side of the first electrode ring portion 35A of the first electrode portion 32. The insulation 38B is placed on the proximal direction side of the first electrode ring portion 35C of the first electrode portion 32. The transducer mounting portion 27 is inserted through the respective insulation rings 38A and 38B. Furthermore, the ultrasonic transducer includes a back mass 36. The back mass 36 is placed on the proximal direction side of the insulation ring 38B. The piezoelectric elements 31A to 31D, the first electrode portion 32, the second electrode portion 33, and the insulation rings 38A and 38B are pressed toward the distal direction by the back mass 36. Consequently, the piezoelectric elements 31A to 31B, the first electrode portion 32, the second electrode portion 33, and the insulation rings 38A and 38B are held between the horn member 23 and the back mass 36.

Figure 6:
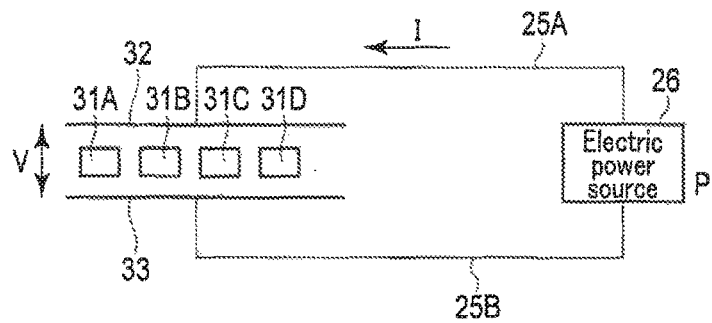
FIG. 6 is a schematic view showing an electrical connection state between the ultrasonic transducer and an electric power source according to the first embodiment.

FIG. 6 is a view showing an electrical connection state between the ultrasonic transducer 22 which is a vibration generating section and the electric power source 26. As shown in FIG. 6, the electric power source 26 is electrically connected to the first electrode portion 32 by the electrical wiring portion 25A. Further, the electric power source 26 is electrically connected to the second electrode portion 33 by the electrical wiring portion 25B. When the vibration generating electric power P is output from the electric power source 26, a vibration generating voltage V is applied between the first electrode portion 32 and the second electrode portion 33. When the vibration generating voltage V is applied, a vibration generating current I flows through the piezoelectric elements 31A to 31D sandwiched between the first electrode portion 32 and the second electrode portion 33. The vibration generating current I is an alternating current whose current direction periodically changes. Furthermore, an ultrasonic impedance value Z which is an impedance value of the vibration generating electric power P is represented by Expression (1).

[Expression 1]

$$Z = V/I = V^2/P \tag{1}$$

As shown in FIG. 2, the sheath 8 is extended from the inside of the tubular case portion 11 toward the distal direction. The sheath 8 includes an inner tubular portion 61 and a movable tubular portion 62 which is provided on an outer peripheral direction side of the inner tubular portion 61. The inner tubular portion 61 is fixed to the rotary operation knob 15, and can rotate around the longitudinal axis C relative to the tubular case portion 11 integrally with the rotary operation knob 15. Furthermore, the movable tubular portion 62 is movable along the longitudinal axis C relative to the tubular case portion 11, the ultrasonic probe 9, and the inner tubular portion 61. Moreover, the movable tubular portion 62 is rotatable around the longitudinal axis C relative to the tubular case portion 11 integrally with the rotary operation knob 15. When a proximal portion of the inner tubular portion 61 and a proximal portion of the movable tubular portion 62 are inserted into the transducer case 21, the sheath 8 is coupled with the transducer case 21 inside the tubular case portion 11. The vibrator case 21 can rotate around the longitudinal axis C relative to the tubular case portion 11 integrally with the rotary operation knob 15 and the sheath 8.

Additionally, in the tubular case portion 11, a ring-shaped support member 73 having elasticity is provided between the inner tubular portion 61 of the sheath 8 and the ultrasonic probe 9 in the radial direction. The support member 73 fixes the ultrasonic probe 9 so that it does not rotate relative to the inner tubular portion 61. That is, the ultrasonic probe 9 is coupled with the sheath 8 through the support member 73. The ultrasonic probe 9 is rotatable around the longitudinal axis C relative to the tubular case portion 11 integrally with the rotary operation knob 15 and the sheath 8.

Inside the tubular case portion 11, a tubular slider portion 63 is provided on an outer peripheral surface of the movable tubular portion 62. The slider portion 63 is movable along the longitudinal axis C relative to the movable tubular portion 62. Au engagement groove 65 is formed in the slider portion 63 along periaxial direction of the longitudinal axis. The movable handle 13 is attached to the tubular case portion 11 through a fulcrum pin 66, and it can turn around the fulcrum pin 66. Further, the movable handle 13 includes an engagement protrusion 67 which can engage with the engagement groove 65 of the slider portion 63. When the engagement protrusion 67 engages with the engagement groove 65, the movable handle 13 is coupled with the slider portion 63. The slider portion 63 can rotate around the longitudinal axis C relative to the tubular case portion 11 and the movable handle 13 integrally with the rotary operation knob 15 and the movable tubular portion 62.

Furthermore, inside the tubular case portion 11, coil spring (a compression coil spring) 68 which is an elastic member is arranged on an outer peripheral surface of the movable tubular portion 62. One end (a distal end) of the coil spring 68 is connected to the movable tubular portion 62. Moreover, the other end (a proximal end) of the coil spring 68 is connected to the slider portion 63. The coil spring 68 is extended along the longitudinal axis C between the movable tubular portion 62 and the slider portion 63 in a reference state where it is contracted by a predetermined contraction amount from a natural state. Additionally, a stopper portion 69 is fixed on the outer peripheral surface of the movable tubular portion 62 on a proximal direction side with respect to the slider portion 63. The stopper portion 69 regulates movement of the slider portion 63 relative to the movable tubular member 62 toward the proximal direction from a state where the slider portion 63 abuts on the stopper portion 69.

Figure 7:
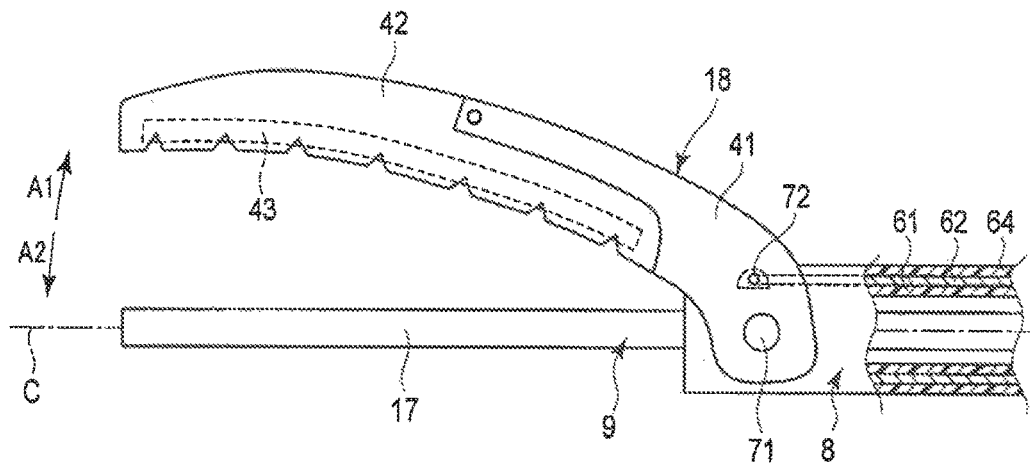
FIG. 7 is a partially sectional side elevation schematically showing a distal portion of a sheath, a treatment section, and a jaw according to the first embodiment.

FIG. 7 is a view showing configurations of the distal portion of the sheath 8, the treatment section 17, and the jaw 18. FIG. 7 shows a state where the jaw 18 is opened relative to the treatment section 17. As shown in FIG. 7, the inner tubular portion 61 and the movable tubular portion 62 are extended toward the distal direction until they reach the distal portion of the sheath 8. The sheath 8 includes an outer tubular portion 64 provided on the outer peripheral direction side of the movable tubular portion 62. The outer tubular portion 64 is fixed to the rotary operation knob 15, and is rotatable around the longitudinal axis C relative to the tubular case portion 11 integrally with the rotary operation knob 15. In a region on the distal direction side with respect to the rotary operation knob 15, the movable tubular portion 62 is covered with the outer tubular portion 64. The jaw 18 is attached to the outer tubular portion 64 of the sheath 8 through a fulcrum pin 71. The jaw 18 is turnable around the fulcrum pin 71 relative to the sheath 8. When the jaw 18 pivots relative to the sheath 8, the jaw 18 opens or closes relative to the treatment section 17. Furthermore, the distal portion of the movable tubular portion 62 is connected to the jaw 18 through a connection pin 72. The jaw 18 can rotate around the longitudinal axis C relative to the tubular case portion 11 integrally with the rotary operation knob 15 and the sheath 8.

When the movable handle 13 is opened or closed relative to the fixed handle 12, an opening or closing operation to open or close the jaw 18 relative to the treatment section 17 is input. That is, the movable handle 13 is an opening or closing operation input section in which the opening or closing operation to open or close the jaw 18 is input. When the opening or closing operation is input, operation force is transmitted to the movable tubular portion 62 through the slider portion 63 and the coil spring 68. Consequently, the movable tubular portion 62 moves relative to the tubular case portion 11 and the ultrasonic probe 9 along the longitudinal axis C. At the time of movement of the movable tubular portion 62, both the slider portion 63 and the coil spring 68 move along the longitudinal axis C integrally with the movable tubular portion 62. When the movable tubular portion 62 moves along the longitudinal axis C, the jaw 18 opens or closes relative to the treatment section 17. That is, an opening direction (a direction of an arrow A1 in FIG. 7) and a closing direction (a direction of an arrow A2 in FIG. 7) of the jaw 18 are perpendicular to (crosses) the longitudinal axis C. That is, when the movable tubular portion 62 moves along the longitudinal axis C integrally with the slider portion 63 and the coil spring 68, an opening angle of the jaw 18 relative to the treatment section 17 varies.

At the time of grasping a treated target such as a biotissue between the treatment section 17 and the jaw 18, when the movable handle 13 is closed relative to the fixed handle 12, the movable tubular portion 62, the slider portion 63, and the coil spring 68 integrally move toward the distal direction. Consequently, the jaw 18 moves toward the closing direction relative to the treatment section 17, and the opening angle of the jaw 18 to the treatment section 17 is reduced. Moreover, when the jaw 18 abuts on the treated target, the movement of the jaw 18 toward the closing direction is stopped, and the movement of the movable tubular portion 62 toward the distal direction is stopped. Even in a state where the movement of the movable tubular portion 62 toward the distal direction is stopped, the movable handle 13 closes relative to the fixed handle 12 and moves relative to the movable tubular unit 62 by the input of the opening or closing operation.

In a state where the movement of the movable tubular portion 62 toward the distal direction is stopped, when the movable handle 13 closes, the slider portion 63 moves toward the distal direction relative to the movable tubular portion 62. Consequently, the coil spring 68 is contracted, and the elastic force of the coil spring 68 is increased beyond that in the reference state. When the elastic force of the coil spring 68 is increased, force which acts on the movable tubular portion 62 from the coil spring 68 is increased. As a result, grasping force for the treated target becomes larger between the jaw 18 and the treatment section 17 than that in the reference state, and a load acting on the treatment section 17 from the jaw 18 is raised.

As described above, an acting state of the load on the treatment section 17 from the jaw 18 varies in accordance with the opening or closing movement of the jaw 18 relative to the treatment section 17 and a state of the treated target held between the jaw 18 and the treatment section 17. Further, in accordance with the acting state of the load on the treatment section 17 from the jaw 18, the movable handle 13 and the slider portion 63 move, and positions of the movable handle 13 and the slider portion 63 with respect to the movable tubular portion 62 change. It is to be noted that, in this embodiment, the movable handle 13, the slider portion 63, and the movable tubular portion 62 form a movement unit which is configured to move in accordance with at least one of the acting state of the load on the treatment section 17 from the jaw 18 and the opening angle of the jaw 18 relative to the treatment section 17. In the movement unit, the opening angle of the jaw 18 relative to the treatment section 17 changes in a state where the movable tubular portion 62 moves integrally with the slider portion 63 in accordance with the movement of the movable handle 13. Furthermore, in a state where the slider portion 63 moves relative to the movable tubular portion 62 in accordance with the movement of the movable handle 13, the acting state of the load on the treatment section 17 from the jaw 18 changes.

Figure 8:
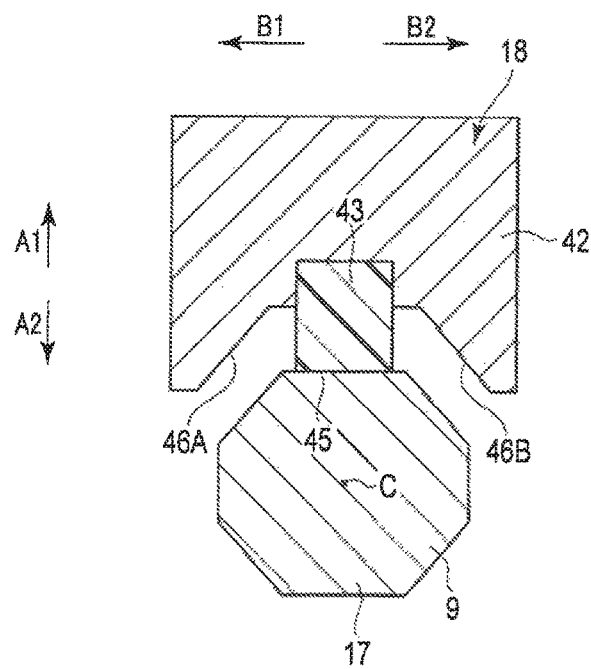
FIG. 8 is a transverse cross-sectional view schematically showing cross sections of the treatment section and the jaw perpendicular to a longitudinal axis according to the first embodiment.

FIG. 8 is view showing configurations of the treatment section 17 and the jaw 18. Here, FIG. 8 shows a state where a treated target is not present between the jaw 18 and the treatment section 17 and the jaw 18 is closed relative to the treatment section 17, and shows a cross section perpendicular to the longitudinal axis C. As shown in FIG. 7 and FIG. 8, the jaw 18 includes a jaw main body 41 whose proximal portion is attached to the sheath 8, and a grasp member 42 attached to the jaw main body 41. The jaw main body 41 and the grip member 42 are formed of, e.g., a metal having electrical conductivity. Additionally, the jaw 18 includes a pad member 43 attached to the grasp member 42. The pad member 43 is made of, e.g., PTFE (polytetrafluoroethylene) having electrical insulation properties.

A contact portion (a contact surface) 45, which is contactable with the treatment section 17 in a state where the jaw 18 is closed relative to the treatment section 17, is formed on the pad member 43. When the jaw 18 is closed relative to the treatment section 17 in a state where no treated target is present between the jaw 18 and the treatment section 17, the abutment portion 45 of the pad member 43 comes into contact with the treatment section 17. The contact portion 45 is opposed to the treatment section 17. Moreover, in this embodiment, the abutment portion 45 is perpendicular to an opening direction (a direction of an arrow A1 in each of FIG. 7 and FIG. 8) and a closing direction (a direction of an arrow A2 in each of FIG. 7 and FIG. 8) of the jaw 18.

Here, two directions which are perpendicular (transverse) to the longitudinal axis C and also perpendicular to the opening and closing directions of the jaw 18 are defined as a first width direction (a direction of an arrow B1 in FIG. 8) and a second width direction (a direction of an arrow B2 in FIG. 8). An inclined facing portion 46A that faces the treatment section 17 in a state where it is inclined relative to the contact portion 45 is formed on the first width direction side of the contact portion 45 by the grasp member 42. Further, an inclined facing portion 46B opposed to the treatment section 17 in a state where it is inclined relative to the abutment portion 45 is formed on the second width direction side of the contact portion 45 by the grip member 42. In a state where the contact portion 45 is in abutment with the treatment section 17, the inclined facing portions 46A and 46E are apart from the treatment section 17. Thus, in a state where the contact portion 45 is in contact with the treatment section 17, the grasp member 42 does not come into contact with the treatment section 17.

As shown in FIG. 3, the control unit 3 includes a control section 51 electrically connected to the electric power source 26. Moreover, the control unit 3 includes an energy operation detector 75, a movement detector 76, and an inspection signal generator 77 which are electrically connected to the control section 51. The energy operation detector 75, the movement detector 76, and the inspection signal generator 77 are electrically connected to each other through an inspection signal circuit K. The inspection signal circuit K is extended to the inside of the handle unit 6 through the inside of the cable 7 and the transducer case 21. It is to be noted that the control section 51 is formed of, e.g., a processor including a CPU (Central Processing Unit) or an ASIC (application specific integrated circuit) or a logic circuit such as an FPGA (Field Programmable Gate Array), and a memory (a storage section). Additionally, each of the energy operation detector 75 and the movement detector 76 is, e.g., a detection circuit. Further, the inspection signal generator 77 functions as a signal output section, and it is, e.g., a signal generation circuit or an analog signal generator.

As shown in FIG. 2 and FIG. 3, inside the handle unit 6, a detection switch (a first switch section) 47 and an energy switch (a second switch section) 48 are provided. The detection switch 47 and the energy switch 48 are electrically connected to each other through the inspection signal circuit K. Further, the detection switch 47 and the energy switch 48 are electrically connected to the energy operation detector 75, the movement detector 76, and the inspection signal generator 77 through the inspection signal circuit K. The detection switch 47 detects a relative position of the movable handle 13 and the movable tubular portion 62 which are a part of the movement unit in the longitudinal axis direction. In this embodiment, the detection switch 47 and the energy switch 48 are provided in a state where they are fixed to the tubular case portion 11. Thus, based on a difference between a position of the movable handle 13 relative to the tubular case portion 11 and a position of the movable tubular portion 62 relative to the tubular case portion 11, the relative position of the movable handle 13 and the movable tubular portion 62 in the longitudinal axis direction is detected. Furthermore, in another embodiment, the detection switch 47 may be fixed to the movable tubular portion 62. In this case, based on a movement amount of the movable handle 13 relative to the movable tubular portion 62, the relative position between the movable handle 13 and the movable tubular portion 62 which are a part of the movement unit along the longitudinal axis direction is detected. When the relative position between the movable handle 13 and the movable tubular portion 62 in the longitudinal axis direction is detected, a moving state of the movement unit (the movable handle 13, the slider portion 63, and the movable tubular portion 62) is detected.

The detection switch 47 which is the first switch section is arranged at a position where it can abut on the movable handle 13, and its opening or closing state is switched in accordance with the opening or closing movement of the movable handle 13. That is, based on moving states of the movable handle 13 and the slider unit 63 which are a part of the movement unit, the opening or closing state of the detection switch 47 changes. In this embodiment, when the movable handle 13 which is an opening or closing operation input section is closed relative to the fixed handle 12 and the movable handle 13 is placed within a prescribed range, the movable handle 13 abuts on the detection switch 47, and the detection switch 47 is closed. At this time, the load that acts on the treatment section 17 from the jaw 18 increases, and the opening angle of the jaw 18 relative to the treatment section 17 decreases. On the other hand, when the movable handle 13 is opened relative to the fixed handle 12 and is not placed within the prescribed range, the movable handle 13 does not come into contact with the detection switch 47, and the detection switch 47 is opened. At this time, the load that acts on the treatment section 17 from the jaw 18 decreases, and the opening angle of the jaw 18 relative to the treatment section increases. Here, when the movement unit is placed within the prescribed range, the movable handle 13 is placed at, e.g., a position where it is closed 5° to 40° or more preferably a position where it is closed 11° to 22° from the fully opened state. Moreover, when the movement unit is placed within the prescribed range, the slider portion 63 moves toward the distal direction by 0.5 mm to 4.0 relative to the movable tubular portion 62, more preferably moves toward the distal direction by 1 mm to 2 mm relative to the movable tubular portion from a state where the slider portion 63 abuts on the stopper portion 69.

With the energy operation input button 16, an energy operation to output a vibration generating electric power P from the electric power source 26 is input. Based on the input the energy operation, the opening or closing state of the energy switch 48 is changed over. In this embodiment, when the energy operation input button 16 is pressed to input the energy operation, the energy switch 48 is closed.

Figure 9:
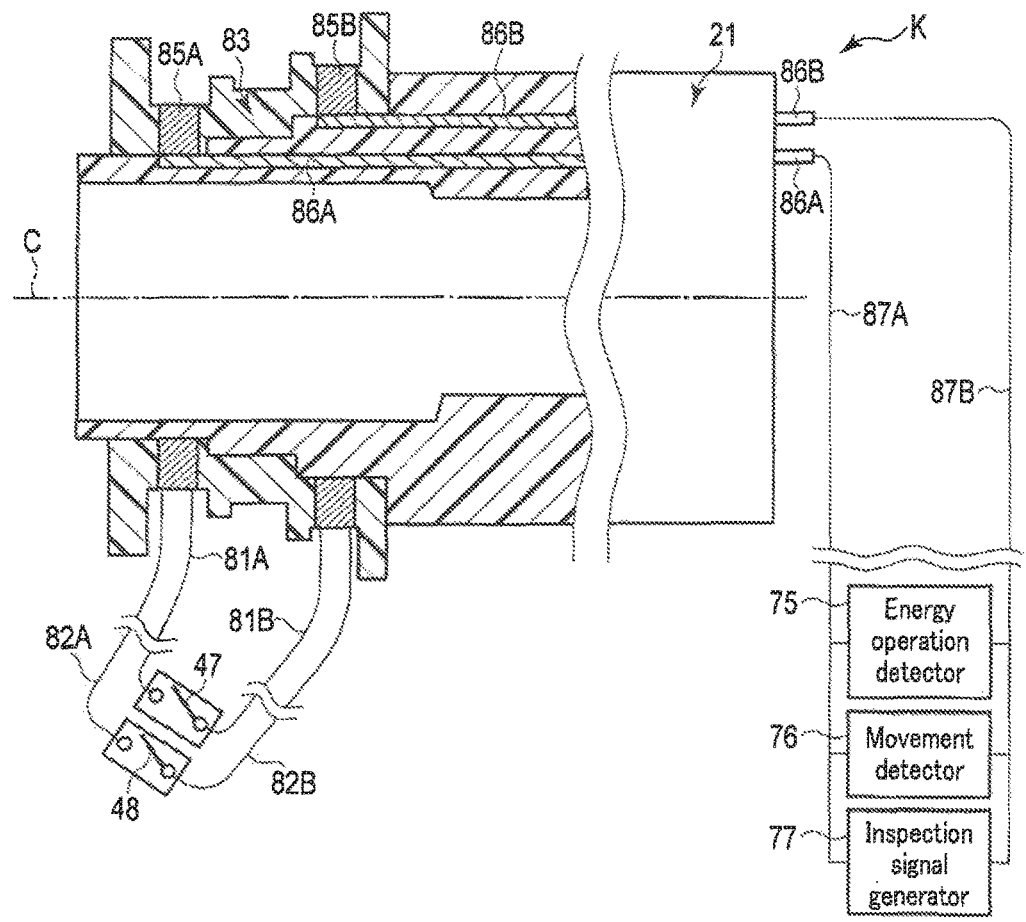
FIG. 9 is a schematic view showing a configuration of an inspection signal circuit according to the first embodiment.

FIG. 9 is a view showing a configuration of the inspection signal circuit K. As shown in FIG. 2 and FIG. 9, one end of each of two electrical signal lines 81A and 81B is connected to the detection switch (the first switch section) 47. Additionally, one end of each of two electrical signal lines 82A and 82B is connected to the energy switch (the second switch section) 48. Inside the tubular case portion 11, an electrical connection ring 83 is provided in a state where it is fixed to the tubular case portion 11. In a state where the transducer unit 5 is coupled with the handle unit 6, a distal portion of the outer peripheral surface of the transducer case 21 abuts on the electrical connection ring 83.

As shown in FIG. 9, ring conductive portions 85A and 85B are formed in the electrical connection ring 83. The ring conductive portions 85A and 85B are electrically insulated from each other. The other end of the electrical signal line 81A and the other end of the electrical signal line 82A are connected to the ring conductive portion 85A. Further, the other end of the electrical signal line 81B and the other end of the electrical signal line 82B are connected to the ring conductive portion 85B. Furthermore, in the transducer case 21, case conducive portions 86A and 86B are extended along the longitudinal axis C. The case conductive portions 86A and 86B are electrically insulated from each other. In a state where the transducer unit 5 is coupled with the handle unit 6, a distal portion of the case conductive portion 86A constantly abuts on the ring conductive portion 85A irrespective of an angle position of the transducer case 21 in a periaxial direction of the longitudinal axis. Similarly, a distal portion of the case conductive portion 86B constantly abuts on the ring conductive portion 85B irrespective of an angle position of the vibrator case 21 in the periaxial direction of the longitudinal axis.

One end of an electrical signal line 87A is connected to a proximal portion of the case conductive portion 86A. The electrical signal line 87A is extended through the inside of the cable 7, and divaricated into three lines in the control unit 3. Moreover, in the control unit 3, one divaricated line of the electrical signal line 87A is connected to the energy operation detector 75, another divaricated line of the same is connected to the movement detector 76, and a remaining line is connected to the inspection signal generator 77. One end of an electrical signal line 87B is connected to a proximal portion of the case conducive portion 86B. The electrical signal line 87B is extended through the inside of the cable 7, and divaricated into three lines in the control unit 3. Additionally, in the control unit 3, one divaricated line of the electrical signal line 87B is connected to the energy operation detector 75, another divaricated line of the same is connected to the movement detector 76, and a remaining line is connected to the inspection signal generator 77.

Figure 10:
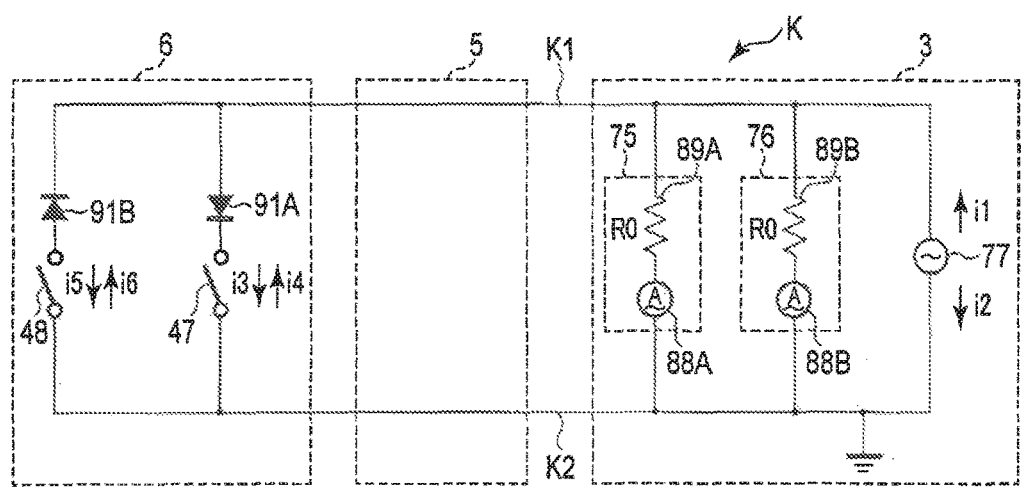
FIG. 10 is a circuit diagram showing an electrical connection state in the inspection signal circuit according to the first embodiment.

FIG. 10 is a view showing an electrical connection state in the inspection signal circuit K. As shown in FIG. 9 and FIG. 10, in the inspection signal circuit K, the electrical signal lines 81A, 82A, and 87A, the ring conductive portion 85A, and the case conductive portion 86A form a first signal path K1, and the electrical signal lines 81B, 82B, and 87B, the ring conductive portion 85B, and the case conductive portion 86B form a second signal path K2. The second signal path K2 is a ground path. The inspection signal generator (the signal output section) 77 generates an alternating current as an analog signal, and outputs the alternating current to the inspection signal circuit K (the detection switch 47 and the energy switch 78). Thus, an output state of the analog signal periodically changes between a state where the alternating current is output from the inspection signal generator 77 toward the first signal path K1 (toward a direction of an arrow I1 in FIG. 10) and a state where the alternating current is output from the inspection signal generator 77 toward the second signal path K2 (toward a direction of an arrow i2 in FIG. 10).

In the inspection signal circuit K, the detection switch 47, the energy switch 48, the energy operation detector 75, and the movement detector 76 are electrically arranged in parallel. The energy operation detector 75 includes a current measuring section 88A which measures a passing current, and a resistor 89A. The current measuring section 88A measures a current which passes through the energy operation detector 75 in a state where an analog signal is output from the inspection signal generator 77. Based on a measurement result in the current measuring section 88A, the energy operation detector 75 detects an opening or closing state of the energy switch 48 and also detects input of an energy operation. Thus, based on a physical quantity of the analog signal, the opening or closing state of the energy switch (the second switch section) 48 is detected.

Further, the movement detector 76 includes a current measuring section 88B which measures a passing current, and a resistor 89B. The current measuring section 88B measures a current passing through the movement detector 76 in a state where an analog signal is output from the inspection signal generator 77. Based on a measurement result in the current measuring section 88B, the movement detector 76 detects an opening or closing state of the detection switch 47, and also detects a moving state of the movement unit (especially, the movable handle 13 and the slider portion 63). Thus, based on a physical quantity of the analog signal, the opening or closing state of the detection switch (the first switch section) 47 is detected. It is to be noted that each of the current measuring sections 88A and 88B is, e.g., an alternating-current ammeter. Furthermore, in this embodiment, the resistor 89 has the same resistance value R0 as that of the resistor 89B.

In the inspection signal circuit K, a diode 91A is electrically arranged in series with the detection switch 47. At the diode 91A, resistance becomes substantially 0 relative to a current flowing from the first signal path K1 toward the second signal path K2 (flowing toward a direction of an arrow 13 in FIG. 10), but the resistance reaches an infinite value relative to a current flowing from the second signal path K2 toward the first signal path K1 (flowing toward a direction of an arrow i4 in FIG. 10). Furthermore, in the inspection signal circuit K, a diode 91B is electrically arranged in series with the energy switch 48. At the diode 91B, the resistance reaches an infinite value relative to a current flowing from the first signal path K1 toward the second signal path K2 (flowing toward a direction of an arrow i5 in FIG. 10), but the resistance becomes substantially 0 relative to a current flowing from the second signal path K2 toward the first signal path K1 (flowing toward a direction of an arrow i6 in FIG. 10).

Figure 11:
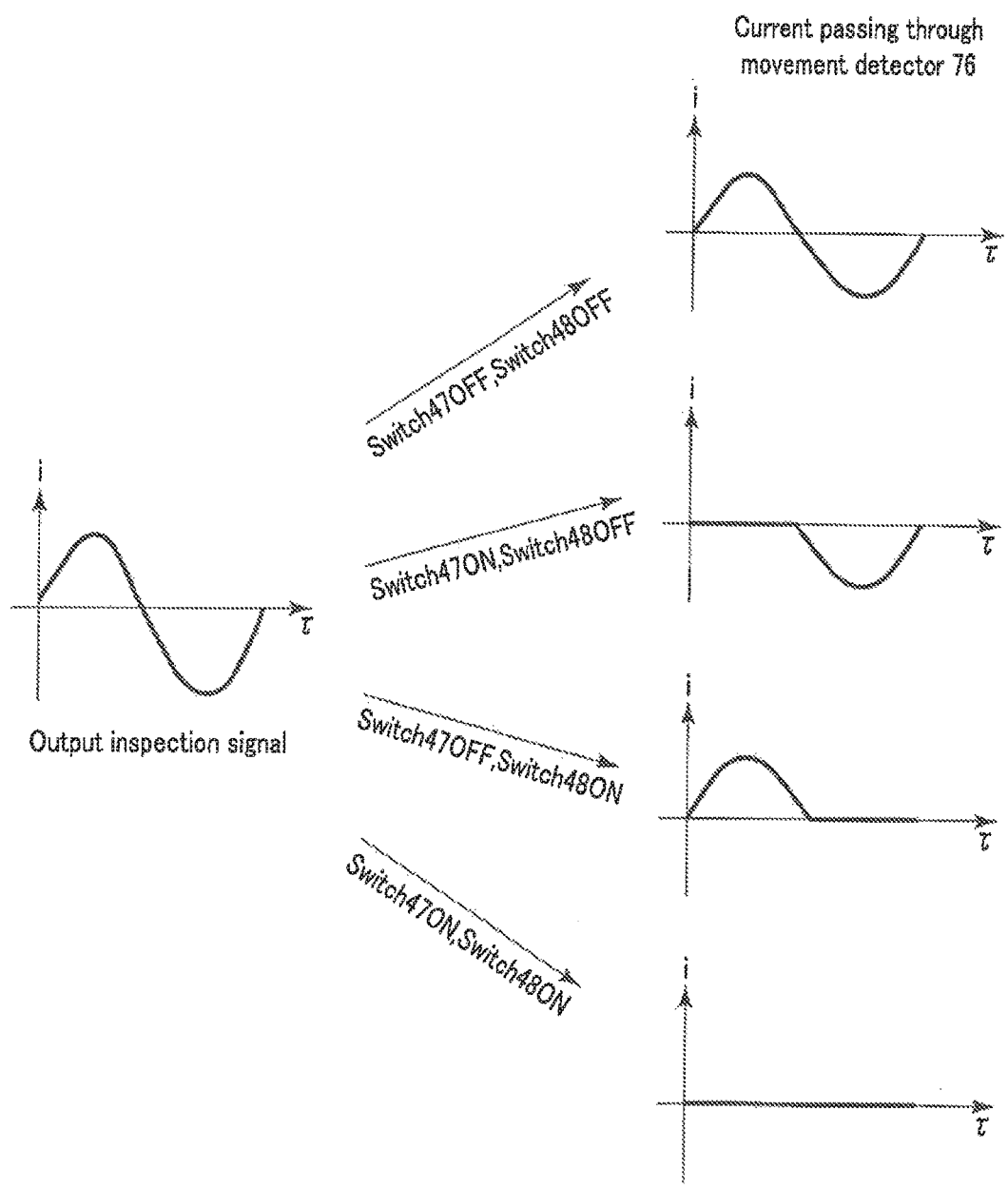
FIG. 11 is a schematic view explaining changes in a current passing through a movement detector relative to an alternating current generated bar an inspection signal generator according to the first embodiment.

FIG. 11 is a view explaining changes in a current (an analog signal) passing through the movement detector 76 relative to an alternating current (an analog signal) generated by the inspection signal generator 77. It is to be noted that the current passing through the movement detector 76 will be described below, and a current passing through the energy operation detector 75 also changes relative to the alternating current generated by the inspection signal generator 77 like the current passing through the movement detector 6. In each of graphs shown in FIG. 11, an axis of abscissa represents an elapsed time τ, and an axis of ordinate represents a current (an analog signal) i. The current i is represented as a positive current when it is output from the inspection signal generator 77 toward the first signal path K1 (toward the direction of the arrow i1 in FIG. 10), and represented as a negative current when it is output from the inspection signal generator 77 toward the second signal path K2 (toward the direction of the arrow i2 in FIG. 10).

As shown in FIG. 11, in the inspection signal generator 77, an analog signal having a waveform of a sin wave (an alternating current) is generated. When the detection switch 47 is opened (an OFF state) and the energy switch 48 is opened (an OFF state), the current does not pass through the detection switch 47 and the energy switch 48. Thus, the analog signal (the alternating current) output from the inspection signal generator 77 constantly passes through the energy operation detector 75 and the movement detector 76. Thus, when the detection switch 47 is opened and the energy switch 48 is opened, the current passing through the movement detector 76 also has a waveform of the sin wave.

Moreover, when the detection switch 47 is closed (an ON state) and the energy switch 48 is opened (the OFF state), the current does not pass through the energy switch 48. As described above, at the diode 91A, the resistance becomes substantially 0 relative to the current flowing from the first signal path K1 toward the second signal path K2 (flowing toward the direction of the arrow i3 in FIG. 10). Thus, when the analog signal is output from the inspection signal generator 77 toward the first signal path K1, the current passes through the detection switch 47 but does not pass through the energy operation detector 75 and the movement detector 76. On the other hand, at the diode 91A, the resistance reaches an infinite value relative to the current flowing from the second signal path K2 toward the first signal path K1 (flowing toward the direction of the arrow i4 in FIG. 10). Thus, when the analog signal is output from the inspection signal generator 77 toward the second signal path K2, the current does not pass through the detection switch 47 but passes through the energy operation detector 75 and the movement detector 76. Thus, when the detection switch 47 is closed and the energy switch 48 is opened, the analog signal passes through the energy operation detector 75 and the movement detector 76 only in a state where the analog signal is output from the inspection signal generator 77 toward the second signal path K2.

Additionally, in a state where the detection switch 47 is opened (the OFF state) and the energy switch 48 is closed (the ON state), the current does not pass through the detection switch 47. As described above, at the diode 91B, the resistance reaches an infinite value relative to the current flowing from the first signal path K1 toward the second signal path K2 (flowing toward the direction of the arrow i5 in FIG. 10). Thus, when the analog signal is output from the inspection signal generator 77 toward the first signal path K1, the current does not pass through the energy switch 48 but passes through the energy operation detector 75 and the movement detector 76. On the other hand, at the diode 91B, the resistance becomes substantially 0 relative to the current flowing from the second signal path K2 toward the first signal path K1 (flowing toward the direction of the arrow i6 in FIG. 10). Thus, when the analog signal is output from the inspection signal generator 77 toward the second signal path K2, the current passes through the energy switch 48 but does not pass through the energy operation detector 75 and the movement detector 76. Thus, when the detection switch 47 is opened and the energy switch 48 is closed, the analog signal passes through the energy operation detector 75 and the movement detector 76 only in a state where the analog signal is output from the inspection signal generator 77 toward the first signal path K1.

Furthermore, when the detection switch 47 is closed (the ON state) and the energy switch 48 is closed (the ON state), the current can flow through the detection switch 47 in a state where the current flows from the first signal path K1 toward the second signal path K2, and the current can flow through the energy switch 48 in a state where the current flows from the second signal path K2 toward the first signal path K1. Thus, when the analog signal is output from the inspection signal generator 77 toward the first signal path K1, the current passes through the detection switch 47 but does not pass through the energy operation detector 75 and the movement detector 76. Moreover, when the analog signal is output from the inspection signal generator 77 toward the second signal path K2, the current passes through the energy switch 48 but does not pass through the energy operation detector 75 and the movement detector 76. Thus, the analog signal (the alternating current) output from the inspection signal generator 77 does not pass through the energy operation detector 75 and the movement detector 76 on a steady basis.

As described above, based on the waveform of the current passing through the energy operation detector 75 and the waveform of the current passing through the movement detector 76, it is possible to detect the opening or closing state of the detection switch 47 and the opening or closing state of the energy switch.

As shown in FIG. 3, the control unit 3 includes an impedance detecting section 52 which is electrically connected to the electric power source 26 and the controller 51, and a peak detecting section 53 which is electrically connected to the impedance detecting section 52 and the control section 51. The impedance detecting section 52 detects an ultrasonic impedance value Z of the vibration generating electric power P with time in a state where the vibration generating electric power P 26 is output from the electric power source. The peak detecting section 53 detects a peak of the ultrasonic impedance value Z (a target peak) based on changes with time of the detected ultrasonic impedance value Z. The peak detecting section 53 includes a gradual decrease detecting section 55, a tentative peak value holding section 56, and a peak judging section 57. Details of the gradual decrease detecting section 55, the tentative peak value holding section 56, and the peak judging section 57 will be described later. It is to be noted that the impedance detecting section 52 is, e.g., a detection circuit. Moreover, the peak detecting section 53 is formed of, e.g., a processor including a CPU (Central Processing Unit) or an ASIC (application specific integrated circuit) or a logic circuit such as an FPGA (Field Programmable Gate Array), and a memory (a storage section).

Additionally, the control section 3 includes a notifying section 58 such as a buzzer or a lamp. The notifying section 58 is electrically connected to the control section 51. The notifying section 58 notifies that the target peak has been detected. It is to be noted that an explanation of the target peak and a detection method of the target peak will be described later.

A function and an effect of the ultrasonic treatment apparatus 1 will now be described later. At the time of giving a treatment to a treated target such as a biological tissue by using the ultrasonic treatment system 1, the sheath 8, the ultrasonic probe 9, and the jaw 18 are inserted into a body or the like in which a treated target is present. Further, the treatment section 17 and the jaw 18 are moved until the treated target is placed between the jaw 18 opened relative to the treating section 17 and the treatment section 17. Furthermore, when the movable handle 13 is closed relative to the fixed handle 12, the treated target is grasped between the treatment section 17 and the jaw 18.

In this state, an energy operation is input by the energy operation input button 16, an operation signal is transmitted to the control section 51, and output of the vibration generating electric power P from the electric power source 26 begins. When the vibration generating electric power P is supplied, the vibration generating current I is converted into an ultrasonic vibration by the piezoelectric elements 31A to 31D. At this time, the control section 51 controls an output state of the vibration generating electric power P by a constant-current control that maintains (a wave height of) the vibration generating current I constant. Thus, the vibration generating voltage V is adjusted in accordance with changes in ultrasonic impedance value Z so as to realize a state where the vibration generating current I becomes constant.

The ultrasonic vibration generated by the ultrasonic transducer 22 is transmitted to the treatment section 17 through the horn member 23 and the ultrasonic probe 9, and the treatment section 17 longitudinally vibrates. When the treatment section 17 longitudinally vibrates in a state where the treated target is griped between the treatment section 17 and the jaw 18, frictional heat is generated between the treated target and the treatment section 17. The frictional heat enables coagulating and simultaneously incising the treated target.

When a treatment is given to the treated target grasped between the treatment section 17 and the jaw 18, cut-and-divided of the treated target occurs in at least a part of a range of the treated target in the transmitting direction of the ultrasonic vibration. FIG. 12 is a view for explaining the cut-and-divided of the treated target U grasped between the treatment section 17 and the jaw 18 it is to be noted the cut-and-divided occurs over the entire range of the treated target in the transmitting direction (the longitudinal axis direction) of the ultrasonic vibration in some cases, or it occurs only in a part of the range of the treated target in the transmitting direction (the longitudinal axis direction) of the ultrasonic vibration in some cases. In a region where the cutoff has occurred, the treatment target U is divided at a dividing plane D that is parallel to the transmitting direction of the ultrasonic vibration and also parallel to the opening and closing directions of the jaw (a direction of an arrow A1 in FIG. 12 and a direction of an arrow A2 in FIG. 12). The dividing face D is perpendicular to a first width direction (a direction of an arrow 31 in FIG. 12) and a second width direction (a direction of an arrow 32 in FIG. 12). Thus, in the range where the cut-and-divided has occurred, the treated target U is divided into a region U1 on the first width direction side with respect to the dividing plane D and a region U2 on the second width direction side with respect to the dividing face D.

In the range where the treated target U is divided by the cut-and-divided, the contact portion 45 of the jaw 18 comes into contact with the treatment section 17. When the treatment section 17 vibrates (longitudinally vibrates) by the ultrasonic vibration in a state where the contact portion 45 of the jaw 18 is in contact with the treatment section 17, the contact portion 45 of the jaw 18 is worn. Thus, it is important to appropriately judge whether the treated target U has been cut-and-divided.

Here, the ultrasonic impedance value Z of the vibration generating electric power P changes in accordance with a load to the ultrasonic probe 9, i.e., a load to the ultrasonic transducer 22 connected to the ultrasonic probe 9. FIG. 13 shows an example of changes with time in an ultrasonic impedance value Z from an output start of the vibration generating electric power P from the electric power source 26. In FIG. 13, an axis of ordinate represents the ultrasonic impedance value Z, and an axis of abscissa represents an elapsed time t from an output start of the vibration generating electric power P. Pressing force to the treatment section 17 from the jaw 18 gradually increases up to the vicinity of a time point at which the treated target U is cut-and-divided due to, e.g., changes in a state of the treated target U between the contact portion 45 of the jaw 18 and the treatment section 17. Thus, the ultrasonic impedance value Z gradually increases with time until the treatment target U is cut-and-divided. Here, the term of the gradual increase with time means that the ultrasonic impedance value Z gradually increases as the elapsed time t advances, and it also includes that the ultrasonic impedance value Z gradually increases while including a small increase or decrease of tens of $\Omega$ or less.

When the treated target U is cut-and-divided, since the contact portion 45 of the jaw 18 is placed near the treatment section 17, a surface of the pad member 43 (the contact portion 45) denatures due to frictional heat generated by the ultrasonic vibration of the treatment section 17. Thus, the load to the ultrasonic probe 9 is gradually decreased. Therefore, the ultrasonic impedance value Z gradually decreases subsequent to the vicinity of the time point where the treated target U is cut off. Here, gradually decreasing with time means that the ultrasonic impedance value Z gradually decreases as the elapsed time t advances, and it also includes that the ultrasonic impedance value Z gradually decreases while including a small increase or decrease of tens of Ω or less.

Since the ultrasonic impedance value Z changes due to the cut-and-divided as described above, the ultrasonic impedance value Z becomes a peak (a maximal value) with time in the vicinity of a time point when the treated target U is cut-and-divided (for example, in the vicinity of a time point when the contact portion 45 of the jaw 18 begins to come into contact with the treatment section 17). When the time-dependent peak of the ultrasonic impedance value Z is detected, it can be appropriately judged whether the treated target U has been cut-and-divided. Here, in the example shown in FIG. 13, an ultrasonic impedance value Z1 becomes a target peak which is a peak (peak value) caused due to the cut-and-divided of the treated target U. Further, an elapsed time t1 is a target peak point at which the target peak is produced.

Figure 14:
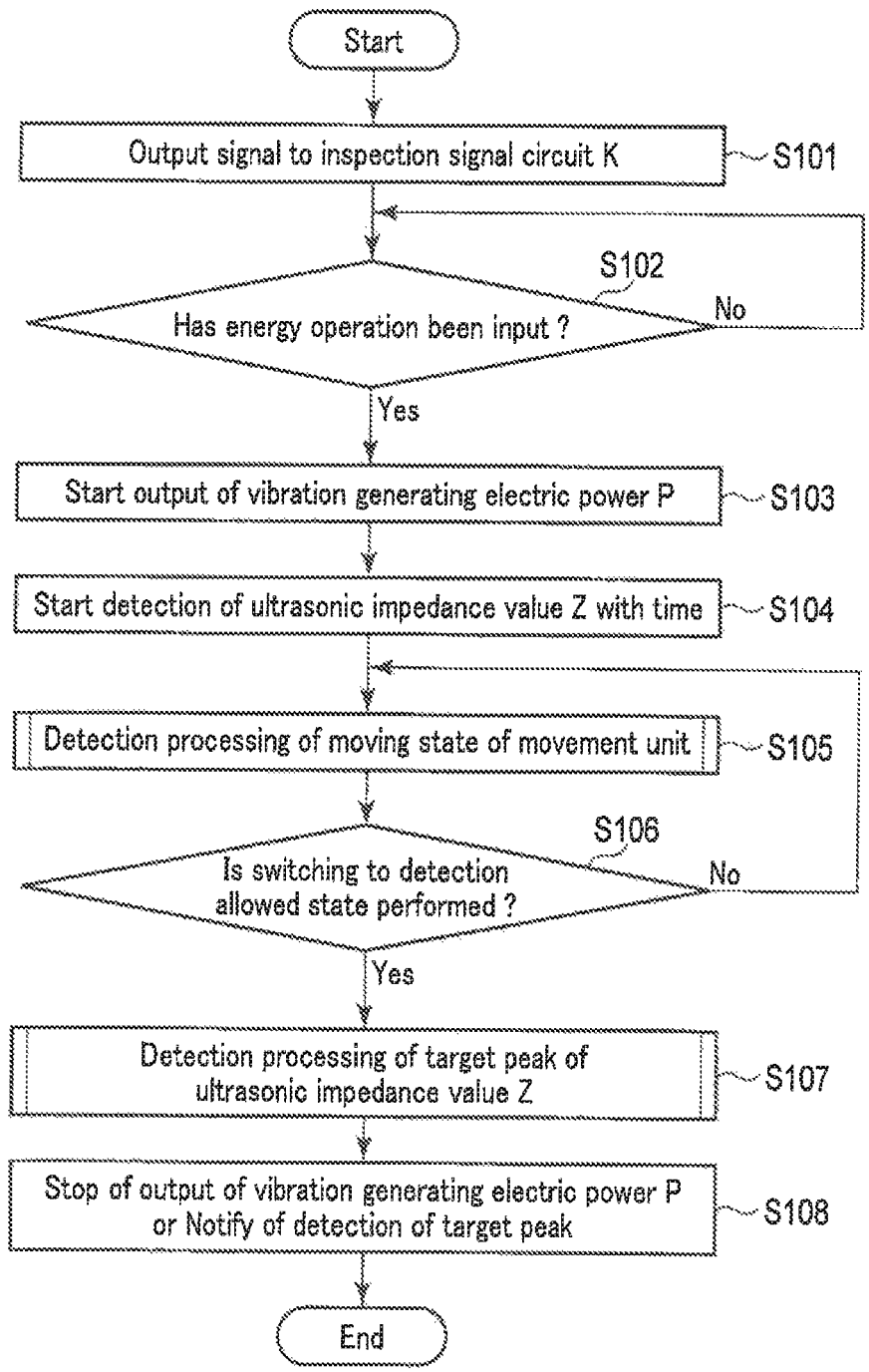
FIG. 14 is a flowchart showing an actuating state in a treatment using the ultrasonic vibration of a control unit according to the first embodiment.

FIG. 14 is a view showing an actuating state of the control unit 3 in a treatment using the ultrasonic vibration. As shown in FIG. 14, at the time of giving a treatment, the analog signal is output from the inspection signal generator 77 to the inspection signal circuit K (a step S101). Furthermore, based on the waveform (a physical quantity) of the current i of the analog signal, the energy operation detector 75 judges whether an energy operation has been input in the energy operation input button 16 (a step S102). As described above, whether the energy operation has been input is judged based on the opening or closing state of the energy switch 48. In this embodiment, when the energy operation is input, the energy switch 48 is closed.

When the input of the energy operation is detected (the step S102—Yes), output of the vibration generating electric power P is started from the electric power source 26 (a step S103). Moreover, the impedance detecting section 52 begins detection of the ultrasonic impedance value Z of the vibration generating electric power P with time (a step S104). Consequently, the ultrasonic impedance value Z is detected with time. For example, when constant-current control to keep a vibration generating current I constant is performed to maintain an amplitude of the ultrasonic vibration constant, changes with time of at least one of the vibration generating electric power P and the vibration generating voltage V are detected. Additionally, based on the detected vibration generating electric power P and/or vibration generating voltage V, the ultrasonic impedance value Z is calculated by using Expression (1). Consequently, the ultrasonic impedance value Z is detected with time. At this time, the peak detecting section 53 (the gradual decrease detecting section 55, the tentative peak value holding section 56, and the peak judging section 57) is controlled to a detection disallowed state where a detection of the target peak is not performed by the control section 51. Further, in a given embodiment, the impedance detecting section 52 detects the vibration generating voltage V and the vibration generating current with time, and calculates the ultrasonic impedance value Z with the use of Expression (1).

Furthermore, the movement detector 76 executes detection processing of a moving state (a moving position) of the movement unit (especially, the movable handle 13 and the slider portion 63) (a step 105). Moreover, based on a detection result in the movement detector 76, the control section 51 judges whether the detection disallowed state is switched to a detection allowed state where the detection the target peak is executed by the peak detecting section 53 (the gradual decrease detecting section 55, the tentative peak value holding section 56, and the peak judging section 57) (a step S106). That is, the control section 51 is configured to control the gradual decrease detecting section 55, the tentative peak value holding section 56, and the peak judging section 57 based on the detection result of the moving state of the movement unit provided by the movement detector 76, and switches between the detection allowed state where the detection of the target peak is executed and the detection disallowed state where the detection of the target peak is not executed.

Figure 15:
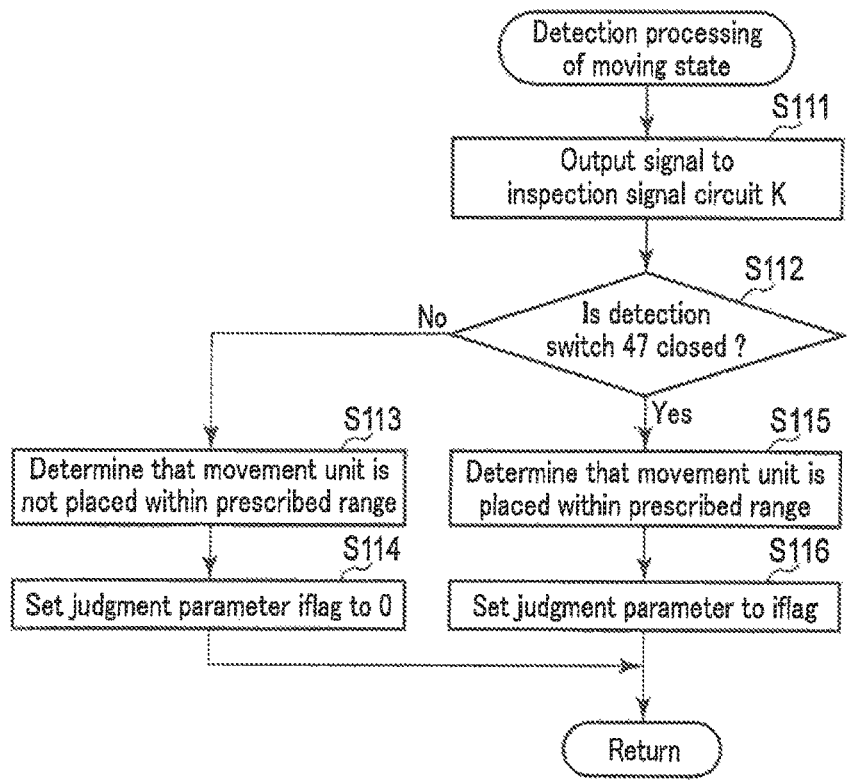
FIG. 15 is a flowchart showing detection processing of a moving state of a movement unit performed by the movement detector according to the first embodiment.

FIG. 15 is a view showing the detecting processing of the moving state of the movement unit executed by the movement detector 76 (the step S105 in FIG. 14). That is, FIG. 15 shows a method of detecting a moving state of the movement unit. As shown in FIG. 15, at the time of detecting the moving state of the movement unit (especially, the movable handle 13 and the slider portion 63), the analog signal is first output from the inspection signal generator 77 to the inspection signal circuit K (a step S111). Further, based on the waveform (a physical quantity) of the current i of the analog signal, the movement detector 76 detects the opening or closing state of the detection switch 47 (a step S112). When the detection switch 47 is opened (the step S112—No), the movement unit is determined not to be placed within the prescribed range (a step S113), and a judgment parameter iflag is set to 0 (a step S114). When the detection switch 47 is closed (the step S112—Yes), the movement unit is determined to be placed within the prescribed range (a step S115), and the judgment parameter iflag is set to 1 (a step S116).

At the step S106 in FIG. 14, based on the judgment parameter iflag, a judgment is made upon whether switching to the detection allowed state is performed. When the judgment parameter iflag is 0, the detection disallowed state is maintained (the step S106—No). On the other hand, when the judgment parameter iflag is 1, the detection disallowed state is switched to the detection allowed state (the step S106—Yes). Thus, when the movement unit is not placed within the prescribed range, the control section 51 controls the peak detecting section 53 (the gradual decrease detecting section 55, the tentative peak value holding section 56, and the peak judging section 57) to the detection disallowed state where the detection of the target peak is not executed. It is to be noted that, in an example shown in FIG. 13, switching to the detection allowed state is performed at an elapsed time t2 before a target peak point t1.

In a treatment, since the movement unit (especially, 13 and 63) is not placed within the prescribed range and the movable handle 13 does not come into contact with the detection switch 47 until the jaw 18 abuts on the treated target U by the closing movement relative to the treatment section 17, the detection switch 47 enters the opened state. Furthermore, the movement unit (especially, 13 and 63) moves to the prescribed range by further closing the movable handle 13 from a state where the movement of the movable tubular portion 62 toward the distal direction stopped due to abutting of the jaw 18 onto the treated target U. Consequently, the movable handle 13 comes into contact with the detection switch 47, and the detection switch 47 enters the closed state. At this time, the coil spring 68 contracts from the reference state by the movement of the slider portion 63 toward the distal direction relative to the movable tubular portion 62, and a load acting on the treatment section 17 from the jaw 18 increases. Thus, based on detecting that the movement unit (especially, 13 and 63) is placed within the prescribed range, an operator can recognize that the load (pressing force) on the treatment section 17 from the jaw 18 increases after the jaw 18 has abutted on the treated target U and incision of the treated target while coagulating the same has started.

Figure 16:
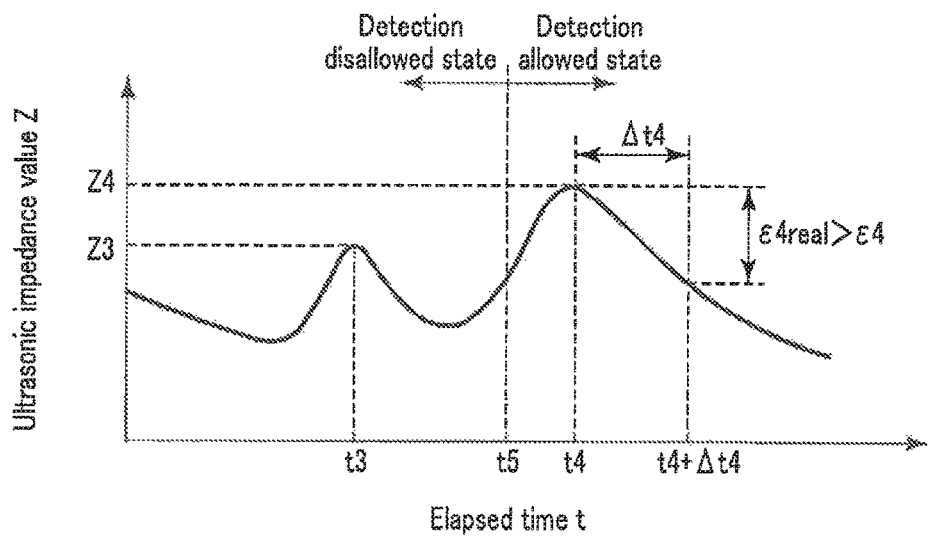
FIG. 16 is a schematic view showing an example of changes with time of the ultrasonic impedance value from the start of the output of the vibration generating electric power from the electric power source according to the first embodiment, which is different from FIG. 13.

FIG. 16 shows an example of changes with time of the ultrasonic impedance value Z after start of output of the vibration generating electric power P from the electric power source 26, which is different from FIG. 13. In FIG. 16, like FIG. 13, an axis of ordinate represents the ultrasonic impedance value Z, and an axis of abscissa represents an elapsed time t from start of output of the vibration generating electric power P. For example, there s a case where the jaw 18 is opened or closed relative to the treatment section 17 while vibrating the treatment section 17 in a treatment depending on surgeons. In this case, the jaw 18 repeats contact with and separation from the treated target U by the opening or closing movement of the jaw 18 in some circumstances. When the jaw 18 repeats contact with and separation from the treated target U, an acting state of a load on the treatment section 17 from the jaw 18 varies. Thus, there is a case where a peak of the ultrasonic impedance value Z is produced due to the contact and the separation of the jaw 8 with and from the treated target U before a target peak caused by cut-and-divided. In an example shown in FIG. 16, at an elapsed time t3, the ultrasonic impedance value Z is detected as a peak (a peak value) Z3 due to the contact and the separation of the contact portion 45 (the jaw 18) with and from the treated target U. Moreover, at an elapsed time t4 after the elapsed time t3, the ultrasonic impedance value Z is detected as a target peak (a target peak value) Z4 due to the cut-and-divided of the treated target U.

As shown in FIG. 16, when the ultrasonic impedance value Z changes with time, at the elapsed time t3, the movement unit (13, 62 and 63) is not placed within the prescribed range. Thus, the detection switch 47 is opened, the judgment parameter if iflag is set to 0, and the detection disallowed state is maintained at the step S106 in FIG. 14. Thus, even if the peak 73 is produced due to the contact and the separation of the contact portion 45 with and from the treated target U, the peak Z3 is determined to be a peak different from the target peak caused by the cutoff. That is, the peak Z3 is not detected as the target peak.

Additionally, after the elapsed time t3, the jaw 18 comes into contact with the treated target U, and incision of the treated target U while coagulating the same is started. Further, at an elapsed time t5 after start of the incision of the treated target while coagulating the same, the movement unit (13, 62, and 63) moves to the prescribed range, and the detection switch 47 is closed. Consequently, the judgment parameter iflag is set to 1, and the detection disallowed state is switched to the detection allowed state at the step S106 in FIG. 14. When switching to the detection allowed state is performed, the target peak Z4 produced at the target peak point t4 after the switching point t5 can be detected.

As shown in FIG. 14, when switching to the detection allowed state is performed at the step S106, the peak detecting section 53 executes the detection processing of the target peak of the ultrasonic impedance value Z caused due to the cut-and-divided of the treated target U based on changes with time of the ultrasonic impedance value Z (a step S107). At this time, the target peak point at which the ultrasonic impedance value Z reaches the target peak (the target peak value) may be detected.

Figure 17:
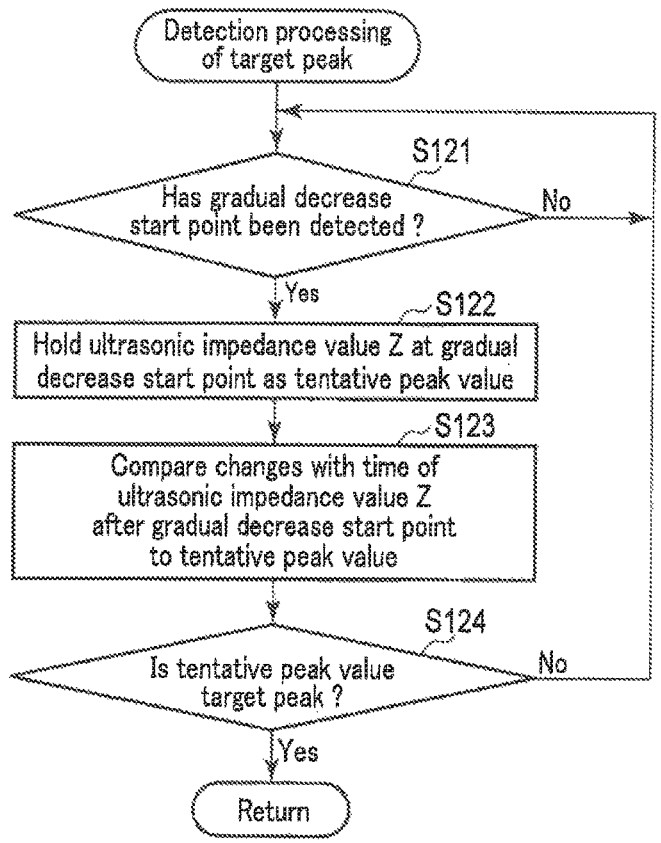
FIG. 17 is a flowchart showing detection processing of a target peak performed by a peak detecting section according to the first embodiment.

FIG. 17 is a view showing the detection processing of the target peak of the ultrasonic impedance value Z executed by the peak detecting section 53 (the step S107 in FIG. 14). That is, FIG. 17 shows a method of detecting the target peak by the peak detecting section 53. As shown in FIG. 17, in the detection processing of the target peak, first, the gradual decrease detecting section 55 detects a gradual decrease start point at which the ultrasonic impedance value Z starts to gradually decrease based detection result of the ultrasonic impedance value Z in the impedance detecting section 52 step S121). The elapsed time t1 is detected as the gradual decrease start point in the example shown in FIG. 13, and the elapsed time t4 is detected as the gradual decrease start point in the example shown in FIG. 16. When the gradual decrease start point is detected (the step S121—Yes), the tentative peak value holding section 56 holds the ultrasonic impedance value Z at the detected gradual decrease start point a tentative peak value (a step S122). The ultrasonic impedance value Z1 at the elapsed time t1 is held as the tentative peak value in the example shown in FIG. 13, and the ultrasonic impedance value Z4 at the elapsed time t4 is held as the tentative peak value in the example shown in FIG. 16.

Furthermore, the peak judging section 57 compares changes with time of the ultrasonic impedance value Z after the gradual decrease start point with respect to the held tentative peak value (a step S123). In the example shown in FIG. 13, changes with time of the ultrasonic impedance value Z after the elapsed time t1 are compared to the ultrasonic impedance value Z1 held as the tentative peak value. In the example s flown in FIG. 16, changes with time of the ultrasonic impedance value Z after the elapsed time t4 are compared to the ultrasonic impedance value Z4 held as the tentative peak value. Moreover, based on the comparison of the changes with time of the ultrasonic impedance value Z with respect to the tentative peak value, the peak judging section 57 judges whether the tentative peak value is the target peak caused due to the cut-and-divided of the treated target U (a step S124). In the example shown in FIG. 13, a judgment is made upon whether the ultrasonic impedance value Z1 held as the tentative peak value is the target peak (the target peak value). In the example shown in FIG. 16, a judgment is made upon whether the ultrasonic impedance value Z4 held as the tentative peak value is the target peak (the target peak value). At this time, whether the detected gradual decrease start point is a target peak point may be judged. It is to be noted that, in the detection disallowed state, control is performed so that at least one of the steps S121 to S124 is not carried out.

In a given example, at the step S123 (the comparison processing) in FIG. 17, whether a decrement $\epsilon$real of the ultrasonic impedance value Z from the tentative peak value is equal to or higher than a reference decrement $\epsilon$ after elapse of a reference time $\Delta T$ from the gradual decrease start point is determined by comparison. Additionally, whether the ultrasonic impedance value Z continuously falls below the tentative peak value after the gradual decrease start point is determined by comparison. In this example, when the decrement $\epsilon$real of the ultrasonic impedance value Z from the tentative peak value is equal to or higher than the reference decrement $\epsilon$ after elapse of the reference time $\Delta T$ from the gradual decrease start point and the ultrasonic impedance value Z continuously falls below the tentative peak value, the tentative peak value determined to be the target peak. In the example shown in FIG. 13, after the gradual decrease start point t1, the ultrasonic impedance value Z continuously falls below the tentative peak value Z1. Further, a decrement $\epsilon$1real of the ultrasonic impedance value Z during elapse of a reference time ΔT1 from the elapsed time t1 which is the gradual decrease start point is equal to or higher than a reference decrement ε1. Thus in the example shown in FIG. 13, the peak judging section 57 determines that the tentative peak value Z1 is the target peak. Therefore, at a time point of the elapsed time t1 (a time point when the tentative peak value Z1 was detected), it is determined that at least a part of the treatment target U has been cut and divided. In the example shown in FIG. 16, the comparison and the judgment are carried out after the elapsed time t4 which is the gradual decrease start point like the example shown in FIG. 13.

Furthermore, in another example, at the step S123, whether the ultrasonic impedance value Z gradually increases after the gradual decrease start point may be judged. Moreover, when the ultrasonic impedance value Z gradually increases after the gradual decrease start point, whether an increment ξreal of the ultrasonic impedance value Z from a gradual increase start point at which gradual increase begins is equal to or higher than a reference increment ξ is judged at the step S123. In this example, when the decrement εreal of the ultrasonic impedance value Z from the tentative peak value is equal to or higher than the reference decrement ε after elapse of the reference time ΔT from the gradual decrease start point and the increment ξreal of the ultrasonic impedance value Z from the gradual increase start point does not become equal to or higher than the reference increment ξ, the tentative peak value is determined to be the target peak. In the example shown in FIG. 13, after the gradual decrease start point t1, the ultrasonic impedance value Z does not gradually increase. Additionally, the decrement ε1real of the ultrasonic impedance value Z during elapse of the reference time ΔT1 is equal to or higher than the reference decrement ε1 without increasing beyond the reference increment ξ from the elapsed time t1 which is the gradual decrease start point. Thus, in the example shown in FIG. 13, the tentative peak value Z1 is determined to be the target peak. In the example shown in FIG. 16, after the elapsed time t4 which is the gradual decrease start point, the comparison and the judgment are carried out like the example shown in FIG. 13.

It is to be noted that, in the foregoing example, a length of the reference time ΔT, a magnitude of the reference decrement ε, and a magnitude of the reference increment ξ are not determined as prescribed values, and they may be set in accordance with, e.g., changes with time of the ultrasonic impedance value Z. Thus, values of the reference time ΔT, the reference decrement ε, and the reference increment ξ change depending on situations. Further, the comparison of changes with time of the ultrasonic impedance value after the gradual decrease start point relative to the tentative peak value (the step S123) and the judgement on whether the tentative peak value is the target peak value (the step S124) are not restricted to the foregoing example.

As described above, when the comparison of changes with time of the ultrasonic impedance value after the gradual decrease start point relative to the tentative peak value (the step S123) and the judgement on whether the tentative peak value is the target peak value (the step S124) are carried out, the target peak caused by the cut-and-divided of the treated target U is detected. The target peak is detected after elapse of the reference time ΔT from the target peak point. Thus, a peak detection point at which the target peak is detected is a time point after the target peak point, and the target peak is not detected at the target peak point at which the ultrasonic impedance value Z reaches the target peak. In the example shown in FIG. 13, the elapsed time t1+ΔT1 is the peak detection point at which the target peak is detected. In the example shown in FIG. 16, the elapsed time t4+ΔT4 is the peak detection point at which the target peak is detected.

When the target peak is detected, in a given example, the output of the vibration generating electric power P from the electric power source 26 is stopped or the output is gradually reduced while performing envelope tracking (ET) by the control section 51 (a step S108). Consequently, the ultrasonic probe 9 no longer longitudinally vibrates, and worn of the contact portion 45 is prevented even if the contact portion 45 of the jaw 18 comes into contact with the treatment section 17. Furthermore, in another embodiment, the notifying section 59 notifies that the target peak has been detected (the step S108). Here, electronic sound is produced when the notifying section 59 is a buzzer, or lighting is performed when the notifying section 59 is a lamp. An operator judges whether the treated target U has been cut-and-divided with the use of the notifying section 59.

In the ultrasonic treatment apparatus 1 according to this embodiment, a gradual decrease start point of the ultrasonic impedance value Z is detected, and the ultrasonic impedance value Z at the gradual decrease start point is held as the tentative peak value. Moreover, changes with time of the ultrasonic impedance value Z after the gradual decrease start point are compared with the tentative peak value to judge whether the held tentative peak value is the target peak which is a detection target. Thus, the target peak can be appropriately detected irrespective of a magnitude of the target peak (a target peak value) produced due to the cut-and-divided. Therefore, in the treatment of the treated target U grasped between the treatment section 17 and the jaw 18 using the ultrasonic vibration, whether the treated target U has been cut and divided can be appropriately judged.

Additionally, in the ultrasonic treatment apparatus 1 according to this embodiment, as described above, even if the peak (e.g., Z3) due to the contact and the separation of the contact portion 45 with and from the treated target U (a change in acting state of a load onto the treatment section 17 from the jaw 18) is produced before the target peak (e.g., Z4), the peak detecting section 53 is controlled to the detection disallowed state at the time of production of the peak (e.g., Z2) due to the contact and the separation of the contact portion 45 with and from the treated target U. Thus, at a time point (e.g., t3) when the peak (e.g., Z3) due to the contact and the separation of the contact portion 45 with and from the treated target U is produced, the peak detecting section 53 does not execute the detection of the target peak. Therefore, even if a peak (e.g., Z3) different from the target peak (e.g., Z4) is produced before the target peak (e.g., Z4), the target peak can be appropriately detected.

(Modification)

It is to be noted that the inspection signal generator 77 generates the analog signal having the waveform of the sin wave (the alternating current) in the foregoing embodiment but an alternating current having a waveform of a square wave or a triangular wave may be generated as the analog signal.

Figure 18:
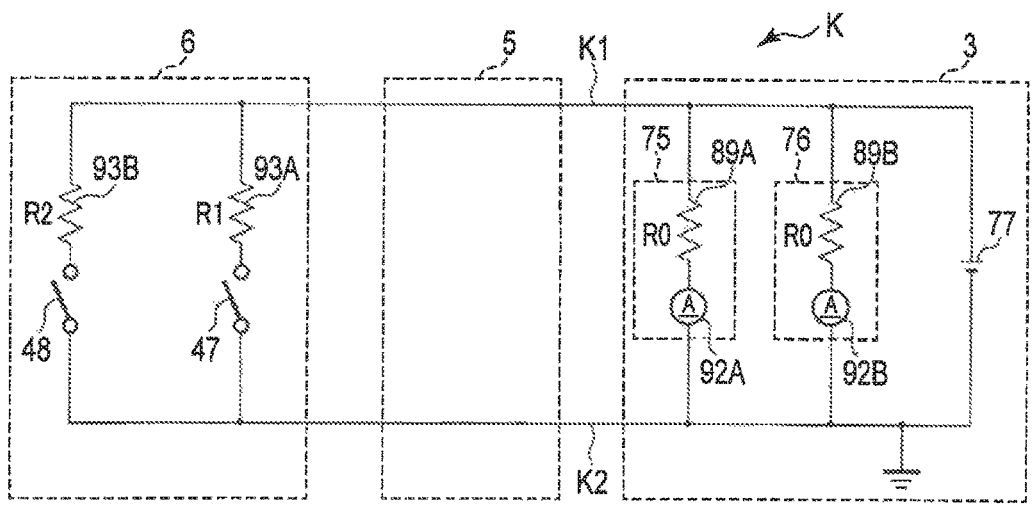
FIG. 18 is a circuit diagram showing an electrical connection state in the inspection signal circuit according to a first modification.

Further, as a first modification, a direct current may be generated as the analog signal by the inspection signal generator 77 as shown in FIG. 18. In this modification, in place of the diode 91A, a resistor 93A is electrically arranged in series with the detection switch 47. Furthermore, in place of the diode 91B, a resistor 93B is electrically arranged in series with the energy switch 48. The resistor 93A has a resistance value R1 different from the resistance value R0 of the resistor 89A of the energy operation detector 75 and the resistor 89B of the movement detector 76. Moreover, the resistor 93B has a resistance value R2 different from the resistance value R0 of the resistor 89A of the energy operation detector 75 and the resistor 89B of the movement detector 76 and the resistance value R1 of the resistor 93A. A current measuring section 92A such as a direct-current ammeter which measures a passing direct current is provided in the energy operation detector 75, and a current measuring section 92B such as a direct-current ammeter which measures a passing direct current is provided in the movement detector 76.

When the inspection signal circuit K is formed as described above, a current value of the current passing through the energy operation detector 75 changes in accordance with the opening or closing state of the energy switch (the second switch section) 48. Likewise, a current value of the current passing through the movement detector 76 changes in accordance with the opening or closing state of the detection switch (the first switch section) 47. Thus, in this modification, likewise, based on a physical quantity of the analog signal, the opening or closing state of the detection switch 47 and the opening or closing state of the energy switch 48 are detected.

Thus, in this modification, likewise, based on the opening or closing state of the detection switch 47, the moving state (a moving position) of the movement unit (the movable handle 13, the slider portion 63, and the movable tubular portion 62) is detected. Consequently, based on the moving state of the movement unit, whether the detection disallowed state is switched to the detection allowed state where the detection of the target peak is performed is appropriately judged.

Further, in the foregoing embodiment, based on a physical quantity of the analog signal, the opening or closing state of the detection switch 47 and the opening or closing state of the energy switch 48 are detected, but it is not restricted thereto. For example, as a second modification, the opening or closing state of the detection switch 47 may be detected based on a signal level of a digital signal (a first digital signal) as shown in FIG. 19. FIG. 19 schematically shows a signal path of the digital signal. In this modification, the movement detector 76 includes a signal generator 95A which outputs a digital signal. The signal generator 95A is an electric power source which functions as a signal output section and generates, e.g., a direct current as the digital signal. The signal generator 95A is electrically connected to the detection switch 47 through a first signal path K'1. Furthermore, the signal generator 95A is electrically connected to the detection switch 47 through a ground path G. It is to be noted that the first signal path K'1 and the ground path G are formed of the electrical signal line (not shown) extended inside the cable 7, the case conductive portion (not shown) of the transducer case 21, the electrical signal line (not shown) extended inside the handle unit 6, and others.

In the detection switch 47, an electrical connection state between the first signal path K'1 and the ground path G varies in accordance with the opening or closing state of the detection switch 47. Moreover, the movement detector 76 includes a voltage detector 98A which detects a voltage (an electric potential difference) between the first signal path K'1 and the ground path G. The voltage detector 98A is e.g., a voltmeter arranged electrically in parallel with the signal generator 95A. Based on a detection result provided by the voltage detector 98A, a signal level of the digital signal (the first digital signal) output from the signal generator 95A is detected.

When the detection switch is opened, the first signal path K'1 is pulled up so that its electric potential becomes higher than that of the ground path G by a power source voltage (e.g., 5 V) of the signal generator 95A. Thus, the signal level of the digital signal becomes a High level (i.e., 1). On the other hand, when the detection switch is closed, the first signal path K'1 is electrically connected to the ground path G at the detection switch 47. Thus, the first signal path K'1 has the same electric potential as the ground path G, and the signal level of the digital signal becomes a Low level (i.e., 0). As described above, in this modification, based on the signal level of the digital signal (the first digital signal) output from the signal generator 95A, the opening or closing state of the detection switch 47 is detected.

In this modification, based on the opening or closing state of the detection switch 47, a moving state (a moving position) of the movement unit (the movable handle 13, the slider portion 63, and the movable tubular portion 62) is detected. Consequently, based on the moving state of the movement unit, whether the detection disallowed state is switched to the detection allowed state where the detection of the target peak is executed is appropriately judged.

Further, in this modifications two energy operation buttons 16A and 16B are provided as energy operation input sections. When an energy operation is input by using the energy operation input button 16A, like the energy operation input button in the first embodiment, the vibration generating electric power P is output from the electric power source 26. Consequently, an ultrasonic vibration is generated by the ultrasonic transducer 22, and the generated ultrasonic vibration is transmitted to the treatment section 17. On the other hand, when an energy operation is input by using the energy operation input button 16B, for example, a high-frequency electric power is output from the electric power source 26. Furthermore, the output high-frequency electric power is supplied to the treatment section 17 and the jaw 18, and the treatment section 17 and the jaw 18 function as electrodes. Moreover, when high-frequency current flows through the treated target U grasped between the treatment section 17 and the jaw 18, the treated target (a biotissue) U is denatured, and the treated target U is coagulated.

In this modification, two energy switches 48A and 48B are provided inside the handle unit 6. The energy switch 48A is closed when an energy operation is input by using the energy operation input button 16A, and the energy switch 48B is closed when an energy operation is input by using the energy operation input button 16B. The energy operation detector 75 includes signal generators 95B and 95C which generate digital signals. The signal generators 95B and 95C function as signal output sections, and have the same configuration as the signal generator 95A of the movement detector 76. The signal generator 95B is electrically connected to the energy switch 48A through a second signal path K'2, and electrically connected to the energy switch 48A through the ground path G. Furthermore, the signal generator 95C is electrically connected to the energy switch 48B through a third signal path K'3, and electrically connected to the energy switch 48B through the ground path G. It is to be noted that the second signal path K'2 and the third signal path K'3 are formed of the electrical signal line (not shown) extended inside the cable 7, the case conductive portion (not shown) of the transducer case 21, the electrical signal line (not shown) extended inside the handle unit 6, and others.

At the energy switch 48A, the electrical connection state between the second signal path K'2 and the ground path G varies in accordance with the opening or closing state of the energy switch 48A. Furthermore, at the energy switch 48B, the electrical connection state between the third signal path K'3 and the ground path G varies in accordance with the opening or closing state of the energy switch 48B. Moreover, the energy operation detector 75 includes a voltage detector 98B which detects a voltage (an electric potential difference) between the second signal path K'2 and the ground path G, and a voltage detector 98C which detects a voltage (an electric potential difference) between the third signal path K'3 and the ground path G. The voltage detectors 98B and 98C have the same configuration as the voltage detector 98A of the movement detector 76. A signal level of a digital signal (a second digital signal) output from the signal generator 95B is detected based on a detection result provided by the voltage detector 98B, and a signal level of a digital signal (the second digital signal) output from the signal generator 95C is detected based on a detection result provided by the voltage detector 98C.

In each of the signal generators 95B and 95C, a relationship between the opening or closing state of the corresponding energy switch (48A or 48B) and the signal level of the digital signal is the same as that of the digital signal (the first digital signal) generated by the signal generator 95A. Thus, based on the signal level of the digital signal (the second digital signal) output from each of the signal generators 95B and 95C, the opening or closing state of the corresponding energy switch (48A or 48B) is detected. Consequently, based on the signal level of the digital signal output from each of the signal generators 95B and 95C, it is possible to detect presence or absence of input of an energy operation using the corresponding energy operation input button (16A or 16B).

It is to be noted that, in case of detecting presence or absence of input of the energy operation based on the signal level of the digital signal, the number of the energy operation input sections (e.g., 16A and 16B) and the corresponding energy switches (e.g., 48A and 48B) can be increased if the number of the signal paths (e.g., K1 to K3) can be in eased inside the cable 7, the transducer case 21, and others. When the number of the energy operation input sections (e.g., 16A and 16B) and the corresponding energy switches (e.g., 48A and 48B) is increased, various energy outputs states can be realized to cope with various treatments.

Figure 20:
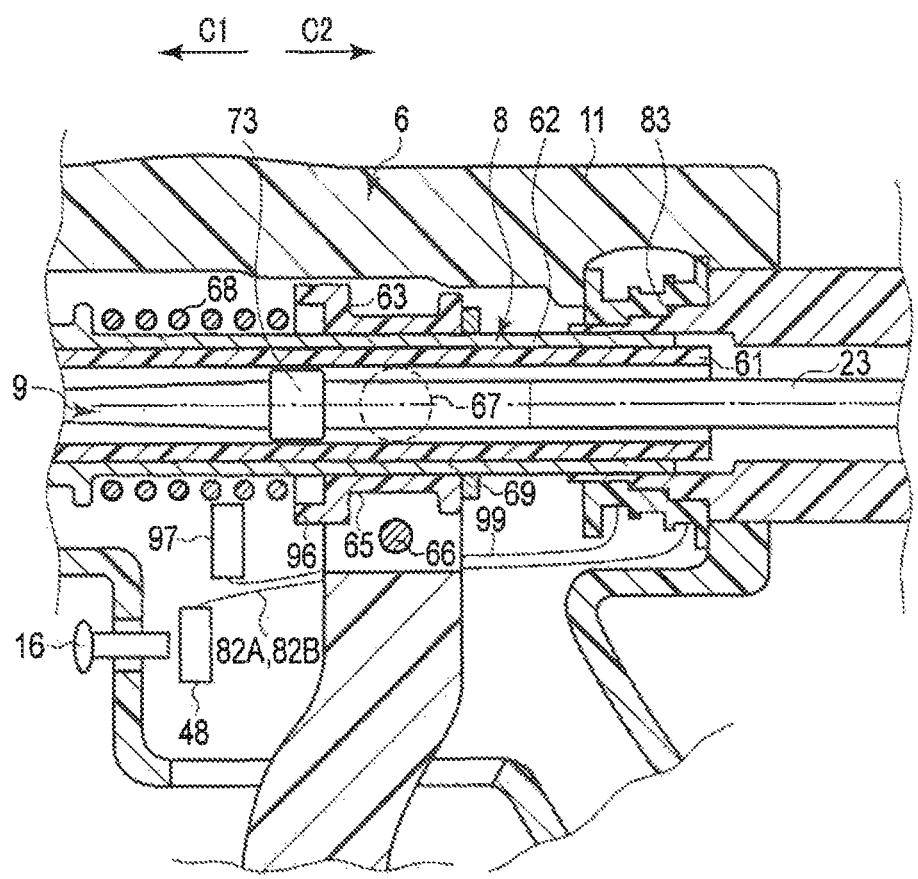
FIG. 20 is a longitudinal cross-sectional view schematically showing configurations of the inside of the handle unit and the inside of the transducer unit according to a third modification

Moreover, in the foregoing embodiments and others, the detection switch 47 is provided, but it is not restricted thereto. For example, as a third modification, a pressure sensor 97 may be provided in place of the detection switch 47 as shown in FIG. 20. The pressure sensor 97 is electrically connected to the movement detector 76 through a signal path 99. A detection signal indicative of a pressure state in the pressure sensor 47 is transmitted to the movement detector 76 through the signal path 99. It is to be noted that the signal path 99 is formed of the electrical signal line (not shown) extended inside the cable 7, the case conductive portion (not shown) of the transducer case 21, the electrical signal line (not shown) extended inside the handle unit 6, and others.

The slider portion 63 forming the movement unit includes a protruding portion 96 which protrudes toward the distal direction. The pressure sensor 97 is arranged at a position where the protruding portion of the slider portion 63 can abut thereon, and a pressing state from the slider portion 63 is changed over in accordance with movement of the slider portion 63. That is, based on a moving state of the movement unit (especially, the movable handle 13 and the slider portion 63), a pressure state of the pressure sensor 97 varies.

In this modification, when the slider portion 63 moves toward the distal direction relative to the movable tubular portion 62 based on the closing movement of the movable handle 13, the slider portion 63 is placed within the prescribed range. In this case, the protruding portion 96 of the slider portion 63 presses the pressure sensor 97, and a pressure in the pressure sensor 97 increases. At this time, a load acting on the treatment section 17 from the jaw 18 grows. On the other hand, when the slider portion 63 moves toward the proximal direction relative to the movable tubular portion 62 by the opening movement of the movable handle 13, the slider portion 63 is no longer placed within the prescribed range. In this case, the slider portion 63 does not come into contact with the pressure sensor 97, and the pressure in the pressure sensor 97 decreases. At this time, the load acting on the treatment section 17 from the jaw 18 is reduced.

As described above, even in this modification, based on the pressure state of the pressure sensor 97, the moving state (the moving position) of the movement unit (especially, the movable handle 13 and the slider portion 63) is detected, and an acting state of the load onto the treatment section 17 from the jaw 18 is appropriately recognized. Consequently, based on the moving state (the acting state of the load onto the treatment section 17 from the jaw 18) of the movement unit, whether the detection disallowed state is switched to the detection allowed state where the detection of the target peak is executed is appropriately judged.

Figure 21:
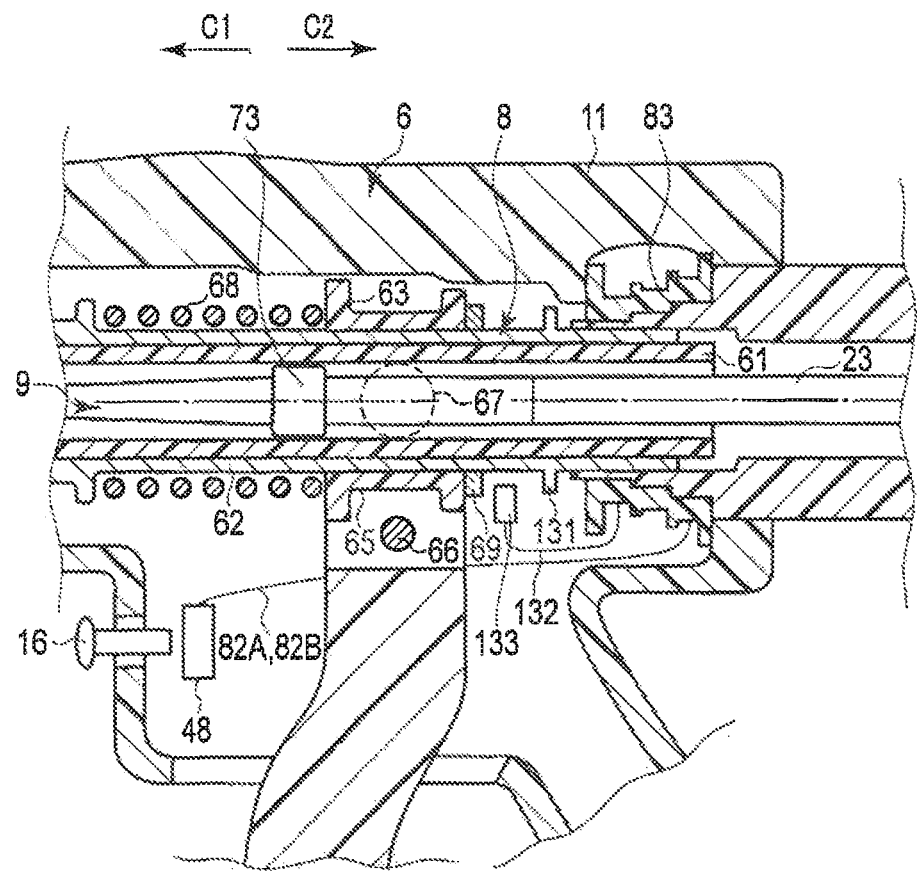
FIG. 21 is a longitudinal cross-sectional view schematically showing configurations of the inside of the handle unit and the inside of the transducer unit according to a fourth modification.

Moreover, in the foregoing embodiment and others, the moving state of the movable handle 13 or the slider portion 63 which moves in accordance with the acting state of the load onto the treatment section 17 from the jaw 18 is detected, but it is not restricted thereto. For example, a fourth modification, the moving state of the movable tubular portion 62 which is a part of the movement unit may be detected as shown in FIG. 21. In this modification, protruding portion 131 which protrudes toward the outer peripheral side is provided to the movable tubular portion 62. Additionally, a pressure sensor 133 is provided inside the tubular case portion 11. The pressure sensor 133 is electrically connected to the movement detector 76 through a signal path 132. A detection signal indicative of a pressure state in the pressure sensor 133 is transmitted to the movement detector 76 through the signal path 132. It is to be noted that the signal path 132 is formed of the electrical signal line (not shown) extended inside the cable 7, the case conductive portion (not shown) of the transducer case 21, and electrical signal line (not shown) extended inside the handle unit 6, and others.

The pressure sensor 133 is arranged at a position where the protruding portion 131 of the movable tubular portion 62 can abut thereon, and a pressing state from the movable tubular portion 62 is changed over in accordance with movement of the movable tubular portion 62. That is, based on the moving state of the movement unit (especially, the movable tubular portion 62), the pressure state to the pressure sensor 133 changes.

In this modification, when the movable tubular portion 62 moves toward the distal direction (integrally with the slider portion 63) by the closing movement of the movable handle 13, the movable tubular portion 62 is placed within the prescribed range. In this case, the protruding portion 131 of the movable tubular portion 62 presses the pressure sensor 133, and a pressure in the pressure sensor 133 increases. At this time, an opening angle of the jaw 18 relative to the treatment section 17 is reduced. On the other hand, when the movable tubular portion 62 moves toward the proximal direction (integrally with the slider portion 63) by the opening movement of the movable handle 13, the movable tubular portion 62 is no longer placed within the prescribed range. In this case, the movable tubular portion 62 does not come into contact with the pressure sensor 133, and the pressure in the pressure sensor 133 is reduced. At this time, the opening angle of the jaw 18 to the treatment section 17 increases.

As described above, in this modification, based on the pressure state of the pressure sensor 133, the moving state (the moving position) of the movement unit (especially, the movable tubular portion 62) is detected, and the opening angle of the jaw 18 relative to the treatment section 17 is appropriately recognized. Consequently, based on the moving state (the opening angle of the jaw 18 relative to the treatment section 17) of the movement unit, whether the detection disallowed state is switched to the detection allowed state where the detection of the target peak is executed is appropriately judged.

Further, in a given modification, after start of outputting the ultrasonic electric power P, adjustment of a frequency f of the ultrasonic vibration may be performed by PLL (Phase Locked Loop) control. In this case, after start of the adjustment at which the adjustment of the frequency f of the ultrasonic vibration is started, detection processing of a minimal value of the ultrasonic impedance value Z is executed. Here, assuming that a time point when a minimal value Z is first detected after the start of the adjustment of the frequency f is a minimal detection point, in this modification, the control section 51 switches the detection disallowed state where the detection of the target peak is not executed the detection allowed state where the detection of the target peak is executed at the minimal detection point. That is, the peak detecting section 53 is controlled to a state where the target peak is not detected until the minimal detection point.

Furthermore, in another modification where the frequency f is adjusted by the PLL control, at the time of startup which is a time point reached after elapse of a predetermined time from the start of the adjustment of the frequency f, the control section 51 may switch the detection disallowed state where the detection of the target peak is not executed to the detection allowed state where the detection of the target peak is executed. That is, in this modification, the peak detecting section 53 is controlled to a state where the target peak is not detected until the time of the startup.

In the foregoing embodiment and others, the ultrasonic treatment apparatus (1) includes the movement unit (13, 62, and 63) which moves in accordance with at least one of the acting state of the load onto the treatment section (17) from the jaw (18) and the opening angle of the jaw (18) relative to the treatment section (17), and the movement detector (76) which is configured to detect the moving state of the movement unit (13, 62, and 63). Moreover, the ultrasonic treatment apparatus (1) includes the impedance detecting section (52) configured to detect the ultrasonic impedance value (Z) of the vibration generating electric power (P) with time in a state where the vibration generating electric power (P) is output from the electric power source (26), the gradual decrease detecting section (55) configured to detect the gradual decrease start point at which the ultrasonic impedance value (Z) starts to gradually decrease based on a detection result of the impedance detecting section (52), the tentative peak value holding section (56) configured to hold the ultrasonic impedance value at the detected gradual decrease start point as a tentative peak value, and the peak judging section (57) configured to judge whether the held tentative peak value is a target peak which is a detection target by comparing changes with time of the ultrasonic impedance value (Z) after the gradual decrease start point with respect to the held tentative peak value. Additionally, the ultrasonic treatment apparatus (1) includes the control section (51) configured to control the gradual decrease detecting section (55), the tentative peak value holding section (56), and the peak judging section (57) to a detection disallowed state where the detection of the target peak is not executed when the movement unit (13, 62, and 63) is not placed within a prescribed range based on a detection result in the movement detector (76).

Reference Example

Further, a first reference example will now be described with reference to FIG. 22. In this reference example, a pressure sensor 135 is provided to the movable handle 13. The pressure sensor 135 is electrically connected to the movement detector 76 through a signal path (not shown). In this reference example, the movement detector 76 functions as an operation force detector configured to detect an operation force acting on the movable handle 13. A detection signal indicative of a pressure state in the pressure sensor 135 is transmitted to the movement detector 76 through the signal path. It is to be noted that the signal path is formed of the electrical signal line (not shown) extended inside the cable 7, the case conductive portion (not shown) of the transducer case 21, the electrical signal line (not shown) extended inside the handle unit 6, and others.

The pressure sensor 135 is arranged at a position where operation force of an operator acts in a closing movement of the movable handle 13 relative to the fixed handle 12. Thus, a pressing state of the pressure sensor 135 is changed over in accordance with an amount of gripping the movable handle 13 by the operator (the operation force from the surgeon). That is, a pressure state to the pressure sensor 135 varies based on the operation force acting on the movable handle.

In this reference example, when the operation force acting on the movable handle 13 by the closing operation of the movable handle 13 increases, the pressure in the pressure sensor 135 grows. At this time, the jaw 18 closes relative to the treatment section 17, and a load acting on the treatment section 17 from the jaw 18 generally increases. On the other hand, when the operation force acting on the movable handle 13 by an opening movement of the movable handle 13 is reduced, the pressure in the pressure sensor 135 decreases. At this time, the jaw 18 opens relative to the treatment section 17, and the load acting on the treatment section 17 from the jaw 18 generally decreases.

As described above, in this reference example, based on the pressure state of the pressure sensor 135, the operation force to the movable handle 13 is detected, and at least one of the load acting the treatment section 17 from the jaw 18 and an opening angle of the jaw 18 relative to the treatment section 17 is appropriately recognized. Consequently, based on an acting state of the operation force to the movable handle 13, whether the detection disallowed state is switched to the detection allowed state where a detection of a target peak is executed is appropriately judged.

That is, the movement detector 76 which functions as the operation force detector detects the operation force acting on the movable handle 13 based on the pressure state in the pressure sensor 135. Further, when the operation force to the movable handle 13 is smaller than a predetermined value, the control section 51 controls the gradual decrease detecting section 55, the tentative peak value holding section 56, and the peak judging section 57 to the detection disallowed state where no detection of the target peak is executed.

Hereinafter, characteristic matters will be added.

Remarks (Added Matter 1)

In an ultrasonic treatment apparatus including vibration generating section configured to generate an ultrasonic vibration when a vibration generating electric power is supplied thereto, a treatment section to which the ultrasonic vibration generated in the vibration generating section is transmitted and which performs a treatment by use of the transmitted ultrasonic vibration, a jaw that is openable and closable relative to the treatment section and includes a contact portion contactable with the treatment section in a state where the jaw is closed relative to the treatment section, an acting state of a load to the treatment section changing in accordance with an opening or closing movement relative to the treatment section, and a movement unit that moves in accordance with at least one of the acting state of the load to the treatment section from the jaw and an opening angle of the jaw relative to the treatment section, a control unit that controls the supply of the vibration generating electric power to the vibration generating section, the control unit comprising:

an electric power source configured to output the vibration generating electric power, an impedance detecting section which is configured to detect an ultrasonic impedance value of the vibration generating electric power with time in a state where the vibration generating electric power is output from the electric power source, a gradual decrease detecting section which is configured to detect a gradual decrease start point to start gradual decrease of the ultrasonic impedance value on the basis of detection results in the impedance detecting section, a tentative peak value holding section which is configured to hold the ultrasonic impedance value at the detected gradual decrease start point as a tentative peak value, a peak judging section which is configured to judge whether or not the held tentative peak value is a target peak of a detection target by comparing, with respect to the held tentative peak value, changes with time of the ultrasonic impedance value after the gradual decrease start point, a movement detector which is configured to detect a moving state of the movement unit, and a control section which is configured to control the gradual decrease detecting section, the tentative value holding section and the peak judging section to a detection disallowed state where a detection of the target peak is not executed, when the movement unit is not placed within a prescribed range based on a detection result of the moving state of the movement unit in the movement detector.

(Added Matter 2)

An ultrasonic treatment apparatus comprising an electric power source configured to output a vibration generating electric power, a vibration generating section configured to generate an ultrasonic vibration when the vibration generating electric power is supplied from the electric power source, a treatment section to which the ultrasonic vibration generated in the vibration generating section is transmitted, and which is configured to perform a treatment by use of the transmitted ultrasonic vibration;

a jaw that is openable and closable relative to the treatment section, and is includes a contact portion contactable with the treatment section in a state where the jaw is closed relative to the treatment section, a movable handle to which an operation to open or close the jaw relative to the treatment section is input, an operation force detector configured to detect an operation force acting on the movable handle, an impedance detecting section which is configured to detect an ultrasonic impedance value of the vibration generating electric power with time, in a state where the vibration generating electric power is output from the electric power source, a gradual decrease detecting section which is configured to detect a gradual decrease start point to start gradual decrease of the ultrasonic impedance value on the basis of detection results in the impedance detecting section, a tentative peak value holding section which is configured to hold the ultrasonic impedance value at the detected gradual decrease start point as a tentative peak value, a peak judging section which is configured to judge whether or not the held tentative peak value is a target peak of a detection target by comparing, with respect to the held tentative peak value, changes with time of the ultrasonic impedance value after the gradual decrease start point, and a control section which is configured to control the gradual decrease detecting section, the tentative value holding section and the peak judging section to a detection disallowed state where a detection of the target peak is not executed, when the operation force is smaller than a predetermined value based on a detection result of the operation force to the movable handle in the operation force detector.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An ultrasonic treatment apparatus comprising:
an electric power source configured to output an electric power;
an ultrasonic transducer configured to generate an ultrasonic vibration by the electric power from the electric power source;
a probe having a distal portion, the ultrasonic vibration generated in the ultrasonic transducer being configured to be transmitted to the distal portion of the probe;
a jaw that is openable and closable relative to the distal portion of the probe;
a movement member configured to move when the jaw is opened or closed relative to the distal portion of the probe;
a processor or a logic circuit configured to:
execute an acquisition of information related to a movement of the movement member;
execute an acquisition of an ultrasonic impedance value of the ultrasonic transducer, the ultrasonic impedance value being acquired based on the electric power supplied from the electric power source to the ultrasonic transducer;
execute a detection of a peak of the ultrasonic impedance value based on an acquisition result of changes with time of the ultrasonic impedance value, the peak being a point at which the ultrasonic impedance value changes from a state where the ultrasonic impedance value increases with time to a state where the ultrasonic impedance value decreases with time;

switch between a disallowed state, where a detection of the peak is not executed, and an allowed state, where a detection of the peak is executed, based on an acquisition result of the movement of the movement member; and execute, when the peak is detected in the allowed state, one of stopping or decreasing an output of the electric power to the ultrasonic transducer and notifying that the peak of the ultrasonic impedance value has been detected.

2. The ultrasonic treatment apparatus according to claim 1, further comprising:

a holdable fixed handle; and a movable handle configured to open or close relative to the fixed handle so as to move the movement member, thereby opening or closing the jaw relative to the distal portion of the probe.

3. The ultrasonic treatment apparatus according to claim 1, further comprising:

a sheath which is extended along a longitudinal axis and in whose distal portion the jaw is turnably attached, the sheath including a movable tubular member configured to open or close the jaw relative to the distal portion of the probe when moving along the longitudinal axis; and an elastic member whose one end is connected to the movable tubular member, wherein the movement member: (i) includes a slider to which the other end of the elastic member is connected, and (ii) expands or contracts the elastic member when moving relative to the movable tubular member, the slider being configured to change an acting state of a load to the distal portion of the probe from the jaw in accordance with a change in an elastic force due to an expansion or a contraction of the elastic member.

4. The ultrasonic treatment apparatus according to claim 1, further comprising a sheath which is extended along a longitudinal axis and in whose distal portion the jaw is turnably attached, wherein the sheath includes a movable tubular member as the movement member, the movable tubular member being configured to change an opening angle of the jaw relative to a treatment section when moving along the longitudinal axis.

5. The ultrasonic treatment apparatus according to claim 1, further comprising: a first switch whose opening or closing state changes in accordance with the movement of the movement member, and a detector configured to detect the movement of the movement member based on the opening or closing state of the first switch.

6. The ultrasonic treatment apparatus according to claim 5, further comprising a signal generator electrically connected to the first switch and configured to output a signal, wherein the detector is configured to detect the opening or closing state of the first switch based on the signal from the signal generator.

7. The ultrasonic treatment apparatus according to claim 6, further comprising a second switch electrically connected to the signal generator and whose opening or closing state changes based on whether an energy operation of outputting the electric power from the electric power source is input, wherein the detector is configured to detect an input of the energy operation based on the opening or closing state of the second switch.

8. The ultrasonic treatment apparatus according to claim 7, wherein the second switch is arranged electrically in parallel with the first switch;

the signal generator is configured to output an analog signal as the signal to each of the first switch and the second switch;

the detector is configured to detect the opening or closing state of the first switch based on a parameter related to the analog signal; and the detector is configured to detect the opening or closing state of the second switch based on the parameter related to the analog signal.

9. The ultrasonic treatment apparatus according to claim 7, wherein the signal generator is configured to: (i) output a first digital signal as the signal to the first switch, and (ii) output a second digital signal, which is different from the first digital signal, as the signal to the second switch;

the detector is configured to detect the opening or closing state of the first switch based on a signal level of the first digital signal; and the detector is configured to detect the opening or closing state of the second switch based on a signal level of the second digital signal.

10. The ultrasonic treatment apparatus according to claim 1, further comprising: a pressure sensor configured to detect a pressure state from the movement member that changes in accordance with the movement of the movement member, and a detector configured to detect the movement of the movement member based on the pressure state detected in the pressure sensor.

11. The ultrasonic treatment apparatus according to claim 1, wherein the processor or the logic circuit is configured to: (i) execute an acquisition of a current supplied to the ultrasonic transducer and a voltage applied to the ultrasonic transducer with time, and (ii) execute an acquisition of the ultrasonic impedance value based on the acquired current and voltage.

12. The ultrasonic treatment apparatus according to claim wherein the processor or the logic circuit is configured to detect a point at which a gradually decreasing start of the ultrasonic impedance value starts on the basis of the acquisition result of the changes with time of the ultrasonic impedance value;

the ultrasonic impedance value at the detected point is a held value; and a variation with time of the ultrasonic impedance value after the detected point is judged to determine whether or not: (i) the ultrasonic impedance value after the detected point, relative to the held value, is more than a predetermined variation, and (ii) the ultrasonic impedance value after the detected point is less than a reference value, thereby judging whether or not the held value is the peak of a detection target.

* * * * *